United States Patent [19]

Hasegawa et al.

[11] Patent Number: 5,380,829
[45] Date of Patent: Jan. 10, 1995

[54] THIOGLYCOSIDE ANALOGS OF GANGLIOSIDES

[75] Inventors: Akira Hasegawa, 1735-160, Ohkurayama, Kano, Gifu-shi, Gifu-ken; Makoto Kiso, Gifu, both of Japan

[73] Assignees: The Nisshin Oil Mills, Ltd., Tokyo; Akira Hasegawa, Gifu, both of Japan

[21] Appl. No.: 842,532

[22] Filed: Feb. 27, 1992

[30] Foreign Application Priority Data

Mar. 29, 1991 [JP] Japan .................. 3-89170

[51] Int. Cl.$^6$ .............................. C07H 5/08
[52] U.S. Cl. .................. 536/4.1; 536/54; 536/17.5; 536/18.2; 536/53; 536/122; 536/123; 514/24
[58] Field of Search ............ 536/41, 17.5, 18.2, 536/53, 54, 122, 123.13; 514/24

[56] References Cited

U.S. PATENT DOCUMENTS

| | | | |
|---|---|---|---|
| 4,229,441 | 10/1980 | Bugianesi et al. | 514/24 |
| 5,019,568 | 5/1991 | Durette et al. | 514/24 |
| 5,077,397 | 12/1991 | Yoshimura et al. | 536/4.1 |

FOREIGN PATENT DOCUMENTS

| | | |
|---|---|---|
| 1-290689 | 11/1989 | Japan . |
| 2-78694 | 3/1990 | Japan . |
| 3-101691 | 4/1991 | Japan . |

OTHER PUBLICATIONS

Kiso et al.; Chemical Abstracts 112:153763g (1990).
(List continued on next page.)

*Primary Examiner*—John W. Hollins
*Assistant Examiner*—Kathleen Kahler Fonda
*Attorney, Agent, or Firm*—Oblon, Spivak, McClelland, Maier, & Neustadt

[57] ABSTRACT

Disclosed are thioglycoside analogs of gangliosides represented by the formula

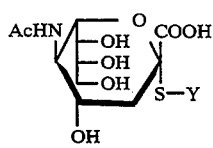

in which Y represents a radical of the following formula

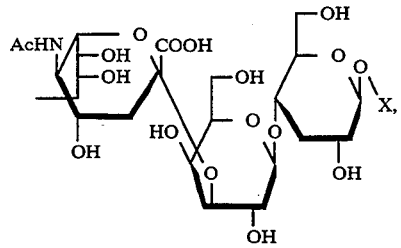

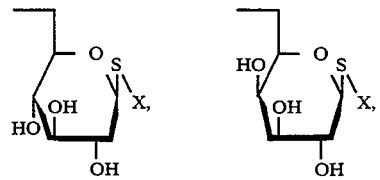

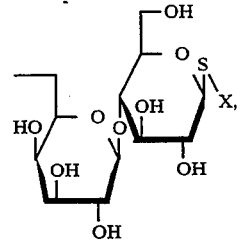

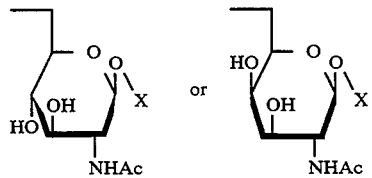

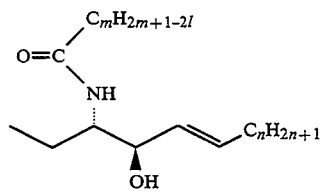

and X represents a radical of the formula wherein m is an integer of 15 to 25, l is an integer of 0 to 3 and n is an integer of 11 to 15. The thioglycoside analogs are expected to exert specific enzyme-inhibitory effects.

8 Claims, No Drawings

OTHER PUBLICATIONS

Hasegawa et al.; Chemical Abstracts 113:231830p (1990).

Hasegawa et al.; J. Carbohydr. Chem. 9(4):369–392 (1990).

Saiensu (Science), vol. 7, 1986, pp. 71–83, S. Hakomori.

Rinsho Byori (Clinical Pathology), vol. XXXIV, No. 11, 1986, pp. 1247–1264, R. Kannagi.

Biochemistry, vol. 22, 1983, pp. 5041–5048, G. Schwarzmann, et al., "Incorporation of Ganglioside Analogues Into Fibroblast Cell Membranes. A Spin–Label Study".

Biochemical And Biophysical Research Communications, vol. 161, No. 2, Jun. 15, 1989, pp. 782–789, M. Nakamura, et al., "Characteristic Incorporation of Ganglioside $GM_3$, Which Induces Monocytic Differentiation in Human Myelogenous Leukemia HL–60 Cells".

Science, vol. 94, No. 2427, 1944, pp. 22–23, G. K. Hirst, "The Agglutination of Red Cells by Allantoic Fluid of Chick Embryos Infected with Influenza Virus".

The Journal of Biological Chemistry, vol. 261, No. 36, Dec. 25, 1986, pp. 17057–17061, Y. Suzuki, et al., "Human Influenza a Virus Hemagglutinin Distinguishes Sialyloligosaccharides in Membrane–Associated Gangliosides as its Receptor Which Mediates the Adsorption and Fusion Processes of Virus Infection".

Glycoconjugate Journal, vol. 7, 1990, pp. 349–356, Y. Suzuki, et al., "New Ganglioside Analogs That Inhibit Influenza Virus Sialidase".

The Journal of Biological Chemisry, vol. 261, No. 30, Oct. 25, 1986, pp. 14278–14282, M. Ito, et al., "A Novel Glycosphingolipid–Degrading Enzyme Cleaves of the Linkage Between the Oligosaccharide and Ceramide of Neutral and Acidic Glycosphinogolipids".

The Journal of Biological Chemistry, vol. 264, No. 16, Jun. 5, 1989, pp. 9510–9519, M. Ito, et al., "Purification and Characterization of Glycosphingolipid–Specific Endoglycosidases (Endoglycoceramidases) From a Mutant Strain of Rhodococcus Sp."

The Journal of Biological Chemistry, vol. 257, No. 21, Nov. 10, 1982, pp. 12752–12756, E. Nudelman, et al., "Characterization of a Human Melanoma–Associated Ganglioside Antigen Defined by a Monoclonal Antibody, 4.2".

Bioshimica Et Biophysixia Acta, vol. 834, 1985, pp. 396–401, M. Kuriyama, et al., "Glycosphingolipids of Leukemic Cells in Adult T–Cell Leukemia–Lymphoma".

Molecular and Cellular Biochemistry, vol. 68, 1985, pp. 3–10, T. N. Seyfried, et al., "Ganglioside $G_{D3}$: Structure, Cellular Distribution, and Possible Function".

THIOGLYCOSIDE ANALOGS OF GANGLIOSIDES

FIELD OF THE INVENTION

This invention relates to thioglycoside analogs of gangliosides which have a wide variety of physiological activities and are expected to exert specific enzyme-inhibitory effects.

BACKGROUND OF THE INVENTION

Glycoconjugates may broadly be classified into three groups, i.e., glycolipid, glycoprotein and proteoglycan. The glycolipid may further be classified into glycoglycerolipid and glycosphingolipid. The latter has attracted widespread attention in recent years and is in active investigation. Glycosphingolipids containing sialic acids are specifically called gangliosides which are known to constitute diverse molecular species depending upon the structure of the saccharide moiety and the lipid moiety. Such molecular diversity of gangliosides is thought to be involved in the modulation of cell growth, differentiation and immunological function; marker molecules for oncogenesis; and receptors for compounds acting on cells, contributing to possible biological roles of gangliosides, which still remains to be determined.

One of the methods for elucidating the function of glycosphingolipids on a molecular level is addition of an exogenous glycosphingolipid, which is simple and convenient to run. It is reported that addition of glycolipids to a cell culture system results in incorporation of the ceramide moiety into the cell membrane [G. Schwarzman et al., Biochemistry, 22, 5041 (1983)]. On the other hand, it is also reported that exogenous ganglioside $GM_3$ added to HL-60 cell culture system is quantitatively incorporated into the cells but is metabolized rapidly to a considerable degree [N. Nakamura et al., Biochem. Biophys. Res. Commun. 161, 782 (1989)]. This means that, with gangliosides, the exogenous molecules are more readily hydrolyzable by sialidase than the endogenous molecules.

In addition, the exogenous molecules are removed by enzymatic treatment in some cases. Therefore, many problems remain to be solved with respect to binding to the membrane, incorporation into cells, metabolism and functional expression of the exogenous molecules.

The hemagglutination reaction with influenza virus found by Hirst [G. K. Hirst, Science, vol. 94, 22 (1944)] suggested the presence of receptors for influenza virus on the cell membrane and the presence of hemagglutinin which recognizes and binds to the receptor, as well as the presence of receptor-destroying enzymes. Later, the receptor-destroying enzymes were found to be sialidases. The hemagglutinin and the sialidase are essential molecular species for establishment of infection and extracellular release of viruses such as adsorption to the receptor, destruction of the receptor, intracellular invasion associated with membrane fusion and liberation of the matured virus from the cell.

Various gangliosides have been used to investigate specific sialosyloligosaccharide structures in receptors recognized by the viruses bearing antigenically different hemagglutinin subtypes and it has been found that the structures are recognized in common despite difference in antigenicity [Y. Suzuki et al., J. Biol. Chem., 261, 17057 (1986)].

Recently, it was elucidated that S-glycoside analogs of gangliosides possessed an inhibitory activity for the influenza virus sialidase [Y. Suzuki et al., Glycoconjugate J. (1990) 7:349–356]. The S-glycoside analogs are said to be non-natural type molecular species since they would not naturally be found even if converted to an O-glycosides. When such S-glycoside analogs are used as a substrate for influenza virus sialidase, they were almost non-hydrolyzable, indicating inhibition of the sialidase. This shows that the S-glycoside analogs may act as competitive inhibitors of sialidase in the presence of $GM_3$-gangliosides. Furthermore, the compound of the following structure was investigated for inhibitory activity against sialidases of different influenza viruses, which was found to exhibit extensive inhibitory activities.

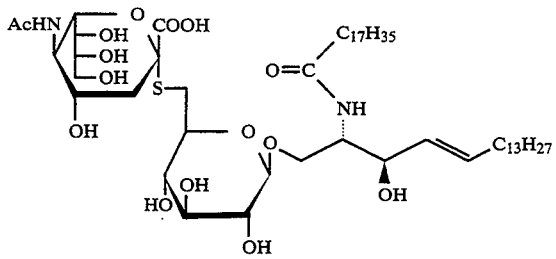

These have suggested that the S-glycoside analogs may be useful for broad-spectrum anti-influenza viral agents which are intended for the inhibition of budding of the virus from host cells. In recent years, an enzyme was discovered which may offer a clue to elucidating the true role of endogenous glycolipids. This enzyme hydrolyzes the glycosidic linkage between the oligosaccharide and ceramide, which is named endo-glycoceramidase [M. Ito et al., J. Biol. Chem., 261, 14278 (1986)]. Studies have been reported on the function of the enzyme, the mode of substrate and the substrate specificity of the enzyme with no report on the true role of endogenous glycolipids [M. Ito et al., J. Biol. Chem., 264, 9510 (1989)]. An inhibitory activity of the S-glycoside analogs of gangliosides for endo-glycoceramidase is expected as that of S-glycoside analogs for sialidases.

Thus the S-glycosides of gangliosides are shown to be inhibitors of the enzyme and they are much expected for their pontential capacities. In this respect, a novel class of S-glycosides is desired.

On one hand, gangliosides occur in living bodies only in a very small quantity and the specimen extracted and purified from living bodies are structurally diversified in the ceramide moiety. A single specimen is difficult to obtain in quantity by extraction. Thus it has been desired to supply a single specimen in large quantities for extensive biochemical studies of gangliosides.

SUMMARY OF THE INVENTION

An object of the invention is to provide new thioglycoside analogs of gangliosides having a wide variety of physiological activities and expected inhibitory activity for enzymes.

Another object of the invention is to provide new class of thioglycoside analogs of gangliosides.

In accordance with the present invention, there is provided a thioglycoside analog of gangliosides represented by the formula

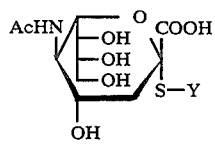

in which Y represents a radical of the following formula

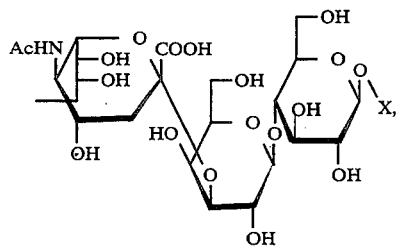

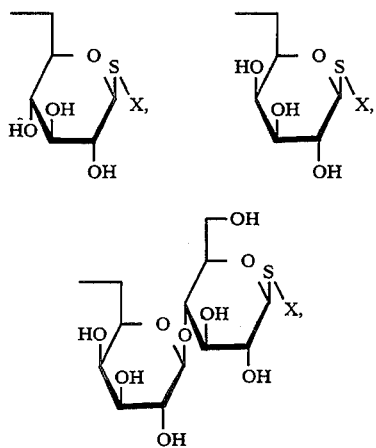

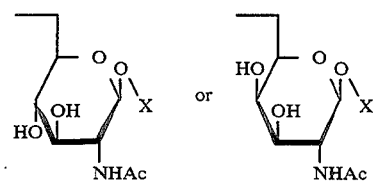

and X represents a radical of the formula

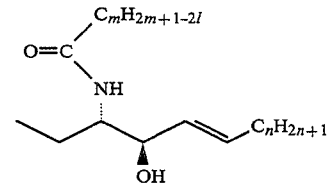

wherein m is an integer of 15 to 25, l is an integer of 0 to 3 and n is an integer of 11 to 15.

DETAILED DESCRIPTION OF THE INVENTION

Preferred examples of the present compounds include those containing the ceramide moiety wherein m is 15–25 (straight chain), l is 0–3 and n is 13 or 15 (straight chain).

Representative examples of the present compounds include Compounds 1 to 6 represented by the following formulas and the analogs thereof wherein the amidated fatty acid radical in the ceramide moiety is derived from a $C_{16-26}$ saturated, or mono-, di- or tri-unsaturated fatty acid and the $C_{13}H_{27}$ moiety in the aminoalcohol is modified to $C_{15}H_{31}$.

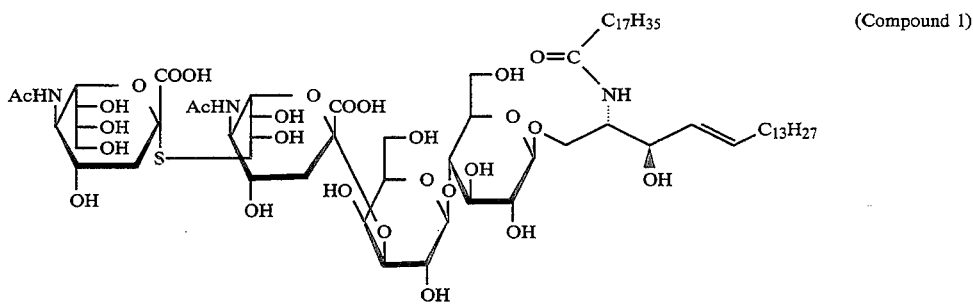

(Compound 1)

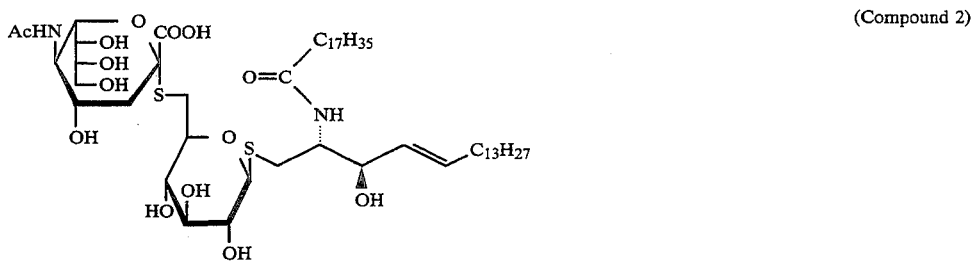

(Compound 2)

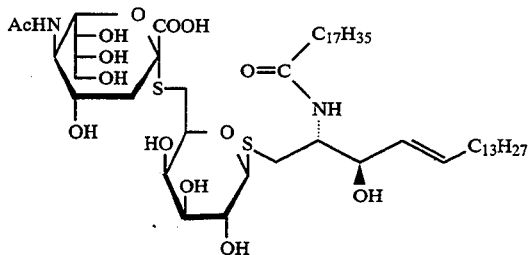

(Compound 3)

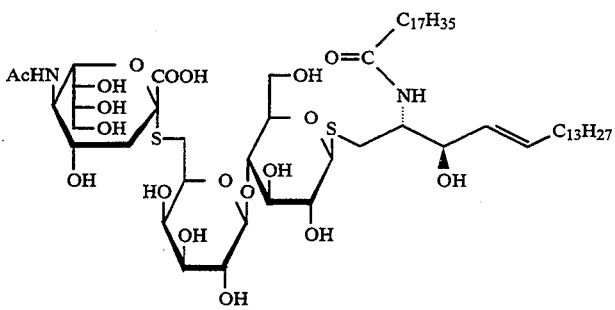

(Compound 4)

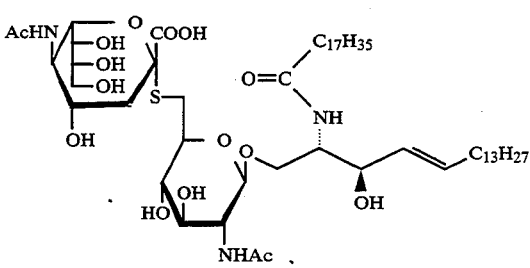

(Compound 5)

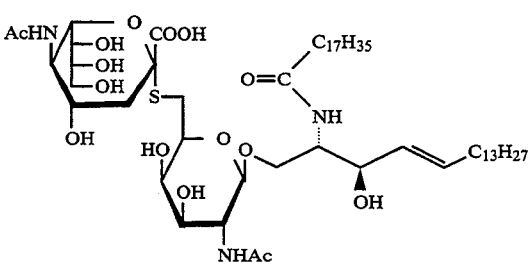

(Compound 6)

Compound 1 is a ganglioside GD₃ analog in which the sialic acid dimer moiety is α-bonded (2→9) through a non-natural type S atom. Ganglioside GD₃ is a ganglioside in human melanoma cells [E. Nucleiman et al., J. Biol. Chem., 257, 12752 (1982)] and human T-cell leukemia cells [N. Kuriyama et al., Biochim. Biophys. Acta., 834, 391 (1985)], which is a cancer-associated antigen. Ganglioside GD₃ has been investigated in detail in relation to changes of gangliosides in the course of a brain development [T. N. Seyfried et al., Mol. Cell. Biochem., 68, 3 (1985)], which is considered to participate in the permeability of cell membrane. Under such circumstances, Compound 1 will serve to elucidate whether the compound possesses ganglioside GD₃-like activities due to the structural change in the sialic acid dimer moiety, finally whether, an α(2→8) bond is required for the activities. If any activity is found in the compound, it may be sustained over a long period of time because decomposition from the non-reducing terminal is not easy.

Compounds 2, 3 and 4 are those in which the ceramide bond in the above-mentioned compounds having an inhibitory activity for influenza virus sialidase is converted to the S-glycoside. Those compounds may exhibit an inhibition of endoglycoceramidase, which will be greatly expected for the elucidation of functions of glycolipids, in addition to the inhibitory activity for sialidase. Furthermore, removal of a sialic acid moiety from these compounds will result in cerebroside or lactosylceramide analogs, which are considered to exhibit new activities due to expected resistance to β-glucocerebrosidase or β-galactocerebrosidase.

Compounds 5 and 6 are those in which sialic acid and the aminosaccharide are bonded through an S-glycoside. Structures in which a sialic acid and an aminosaccharide are α-bonded (2→6) are naturally occurring as a partial structure in a saccharide chain of glycolipids and glycoproteins. However, no compound has been discovered wherein a ceramide is bonded to the aminosaccharide. Thus, Compounds 5 and 6 are expected to be a new physiologically active compound.

It is expected that the ganglioside analogs of the invention will be a specific enzyme inhibitor and offer a clue to the elucidation of the function of glycolipids including gangliosides.

Compound 1 can be prepared in accordance with the following steps. Methyl(5-acetamido-3,5-dideoxy-2-thio-D-glycero-α-D-galacto-2-nonulopyranosid)onate (Compound 7) is reacted with 2,2-dimethoxypropane in N,N-dimethylformamide in the presence of p-toluene-sulfonic acid catalyst, by which the hydroxyl groups at the 8- and 9-positions are protected with an isopropylidene group to provide Compound 8. Compound 8 is acetylated to Compound 9 which is then hydrolyzed at the isopropylidene group with 80% acetic acid solution to afford Compound 10. Then Compound 10 is reacted at 0° C. with carbon tetrabromide and triphenylphosphine in a pyridine solvent to afford Compound 11. This compound is acetylated to Compound 12. Further, Compound 12 is condensed with Compound 13 to form Compound 14 which is then acetylated to Compound 15. Compound 15 is condensed with sodium salt of methyl 5-acetamido-4,7,8,9-tetra-O-acetyl-3,5-dideoxy-2-thio-D-glycero-α-D-galacto-2-nonulopyranosylonate (Compound 16 ) in N,N-dimethylformamide to give a saccharide chain (Compound 17). Subsequently, Compound 17 is deprotected at 2-(trimethylsilyl)ethyl group to form Compound 18 which is then reacted with trichloroacetonitrile in dichloromethane to form the trichloroacetimidate (Compound 19). Compound 19 is condensed with (2S,3R,4E)-2-azido-3-O-benzoyl-4-octadecene-1,3-diol (Compound 20) to form Compound 21. Then the azide group in the compound is reduced with hydrogen sulfide gas to the amino group into which stearic acid is then introduced to form Compound 22. All of the protecting groups are removed to obtain the desired Compound 1. The reaction steps are shown in the following scheme 1.

Compound 2 can be prepared in accordance with the following reaction steps. S-(Methyl 5-acetamido-4,7,8,9-tetra-O-acetyl-3,5-dideoxy-D-glycero-α-D-galacto-2-nonulopyranosylonate)-(2→6)-2,3,4-tri-O-acetyl-6-thio-D-glucopyranose (Compound 23) is reacted with methanesulfonyl chloride and 2,4,6-collidine in dichloromethane to form the α-Cl form which is then reacted with potassium thioacetate in acetone to form the β-SAc form (Compound 24). Compound 24 is reacted with Na to form the β-SNa salt. This salt is reacted with a sphingosine acceptor, (2S,3R,4E)-2-azido-3-O-benzoyl-1-O-(p-toluenesulfonyl)-4-octadecene-1,3-diol (Compound 25) to form Compound 26. The azide group in the compound is reduced with $H_2S$ gas to the $NH_2$ group into which stearic acid is then introduced to form Compound 27 and the protecting groups in the resultant compound are removed to obtain the desired Compound 2. The reaction steps are shown the following scheme 2.

Compound 3 to 5 can be prepared in accordance with similar reaction steps as shown for Compounds 1 and 2, which are shown respectively in the following schemes 3 to 5. Compound 6 may be prepared in a similar manner as shown in the reaction scheme 5.

The analogs of Compounds 1 to 6 wherein the amidated fatty acid in the ceramide moiety is derived from a $C_{16-26}$ saturated, or mono-, di- or tri-unsaturated fatty acid and the $C_{13}H_{27}$ moiety in the aminoalcohol is modified to $C_{15}H_{31}$ may be prepared by the modification of the reaction steps shown in the schemes 1 to 5 depending on the desired compounds.

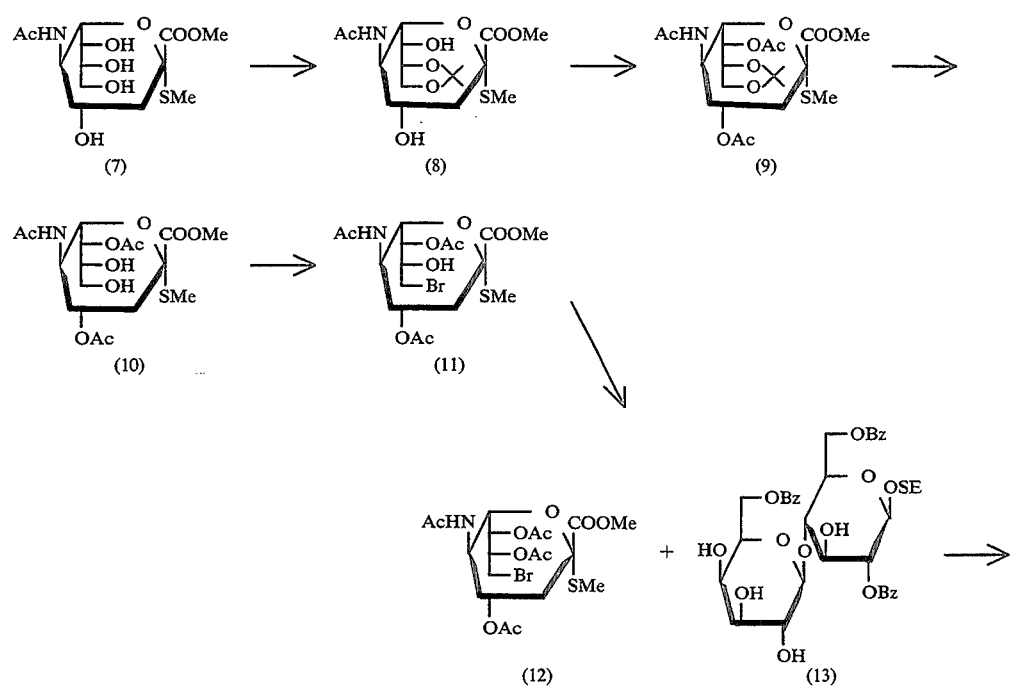

Scheme 1

-continued
Scheme 1
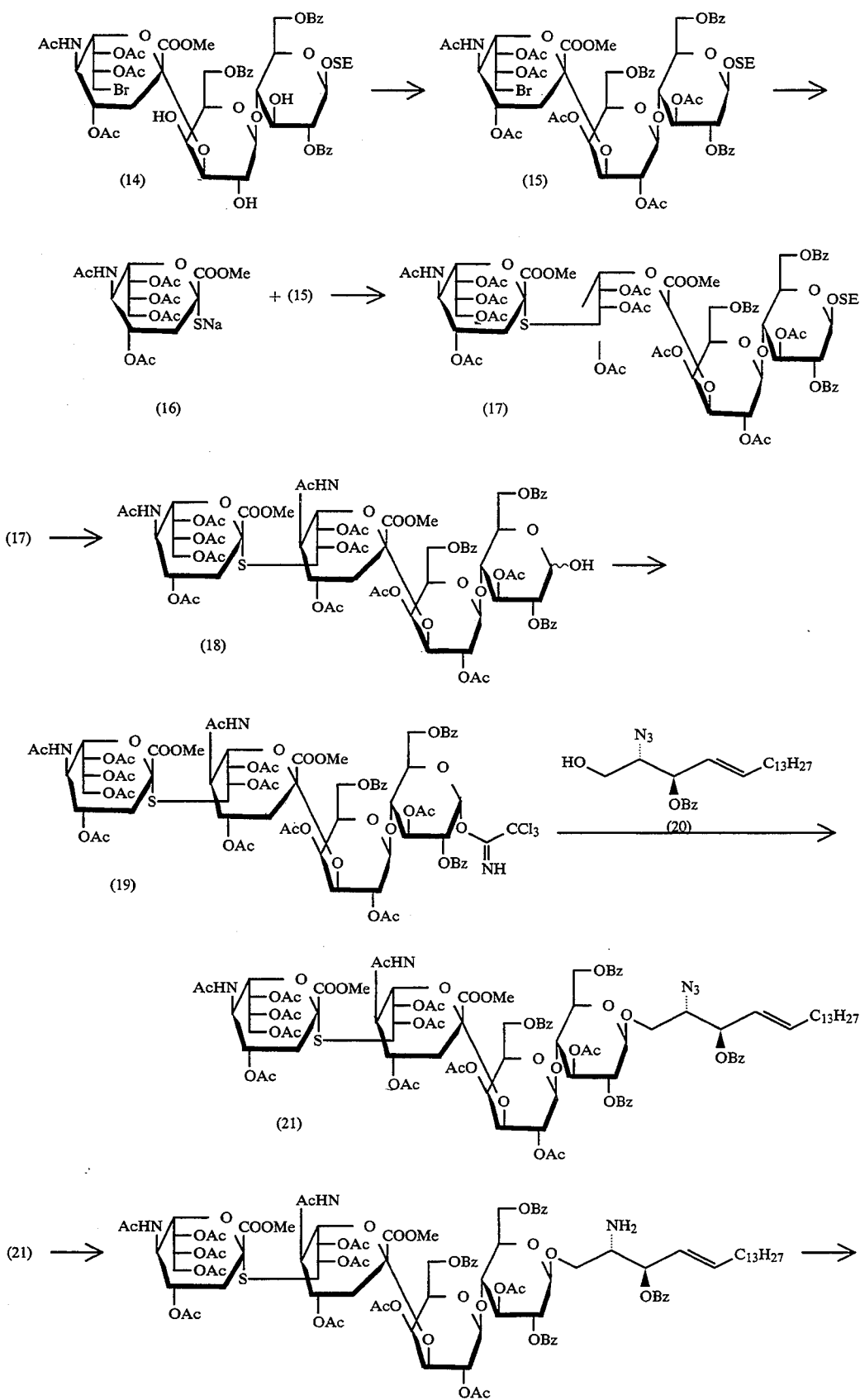

-continued
Scheme 1
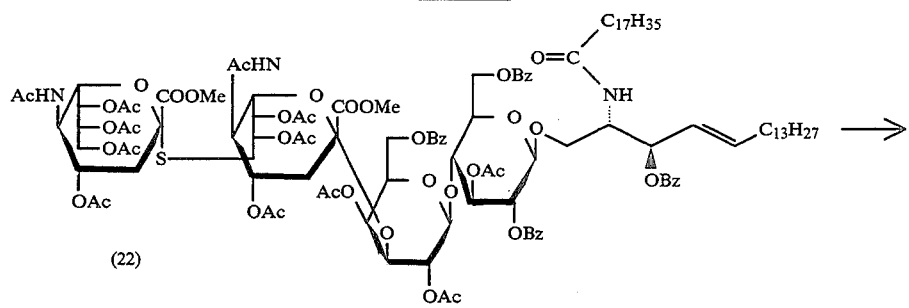
(22)
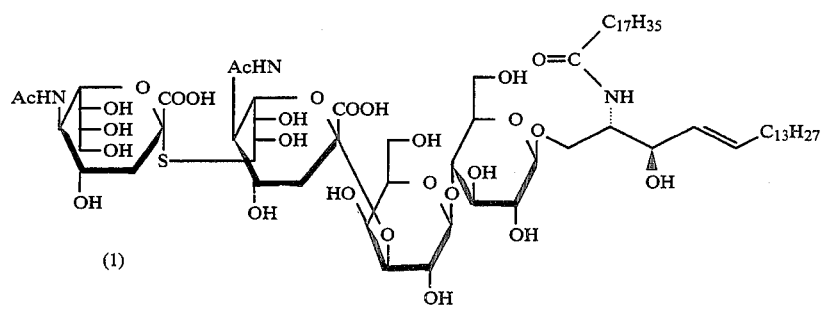
(1)
Scheme 2
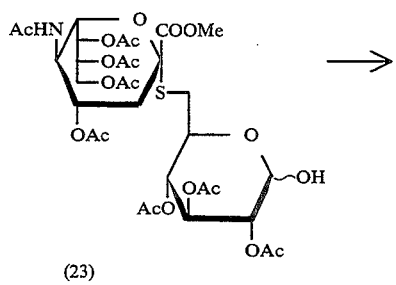
(23)
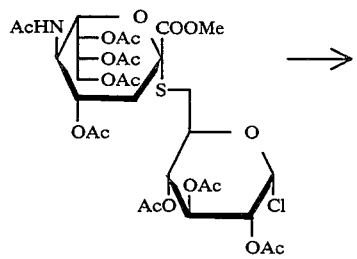
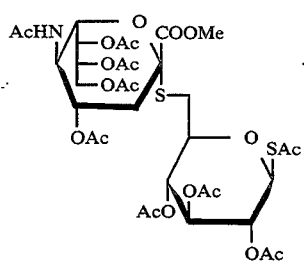
(24)
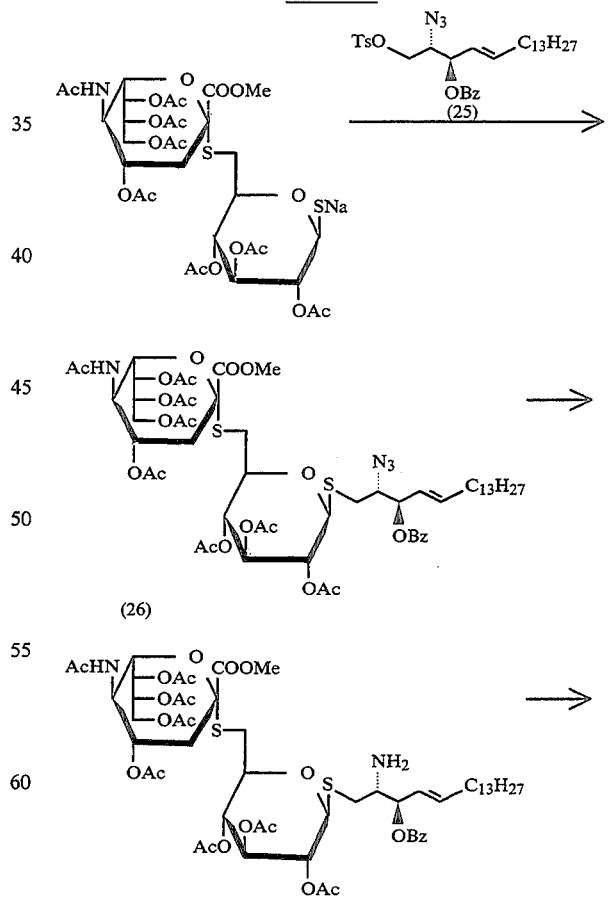

-continued
Scheme 2
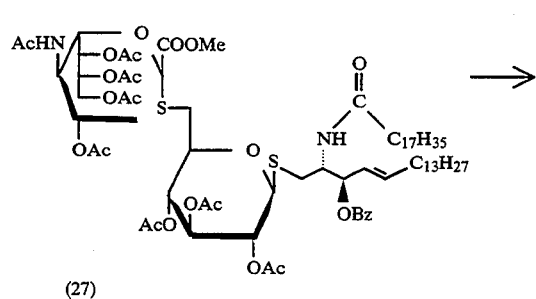
(27)
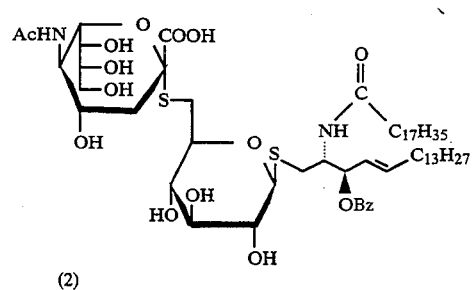
(2)
Scheme 3
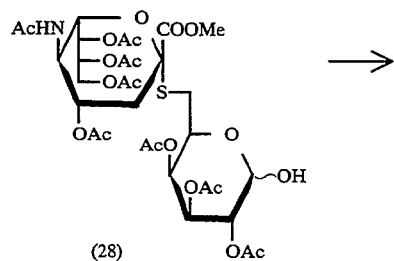
(28)
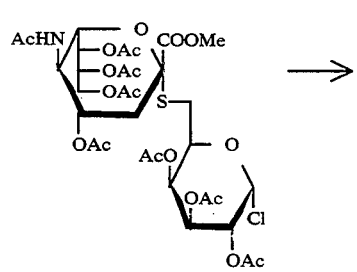
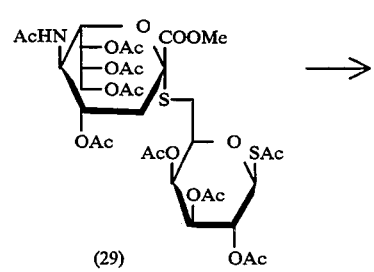
(29)
-continued
Scheme 3
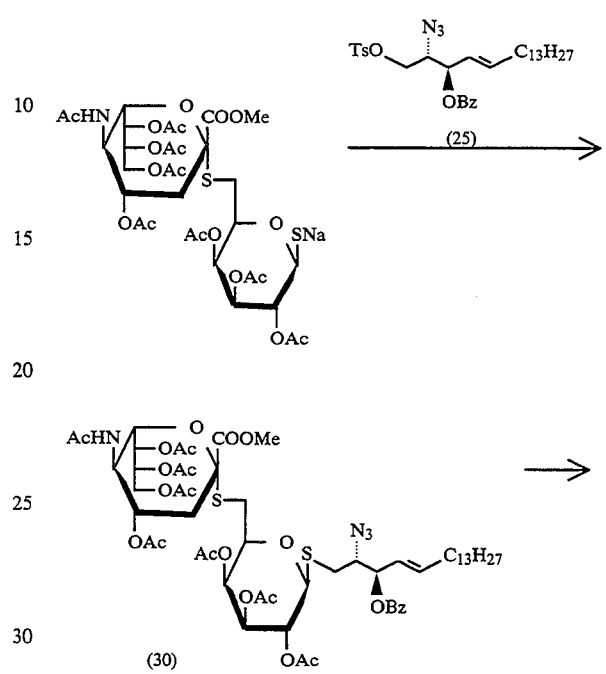
(30)
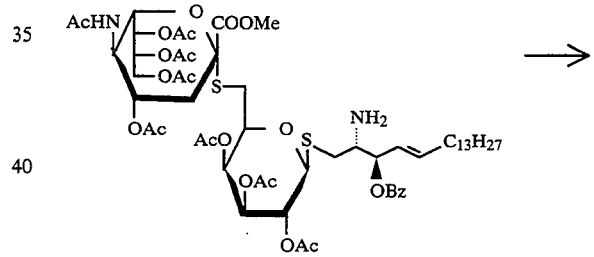
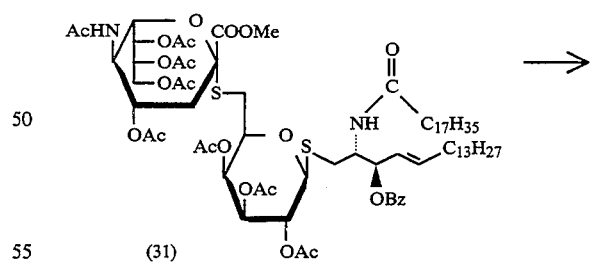
(31)
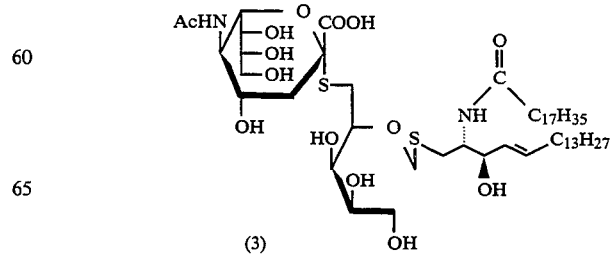
(3)

Scheme 4
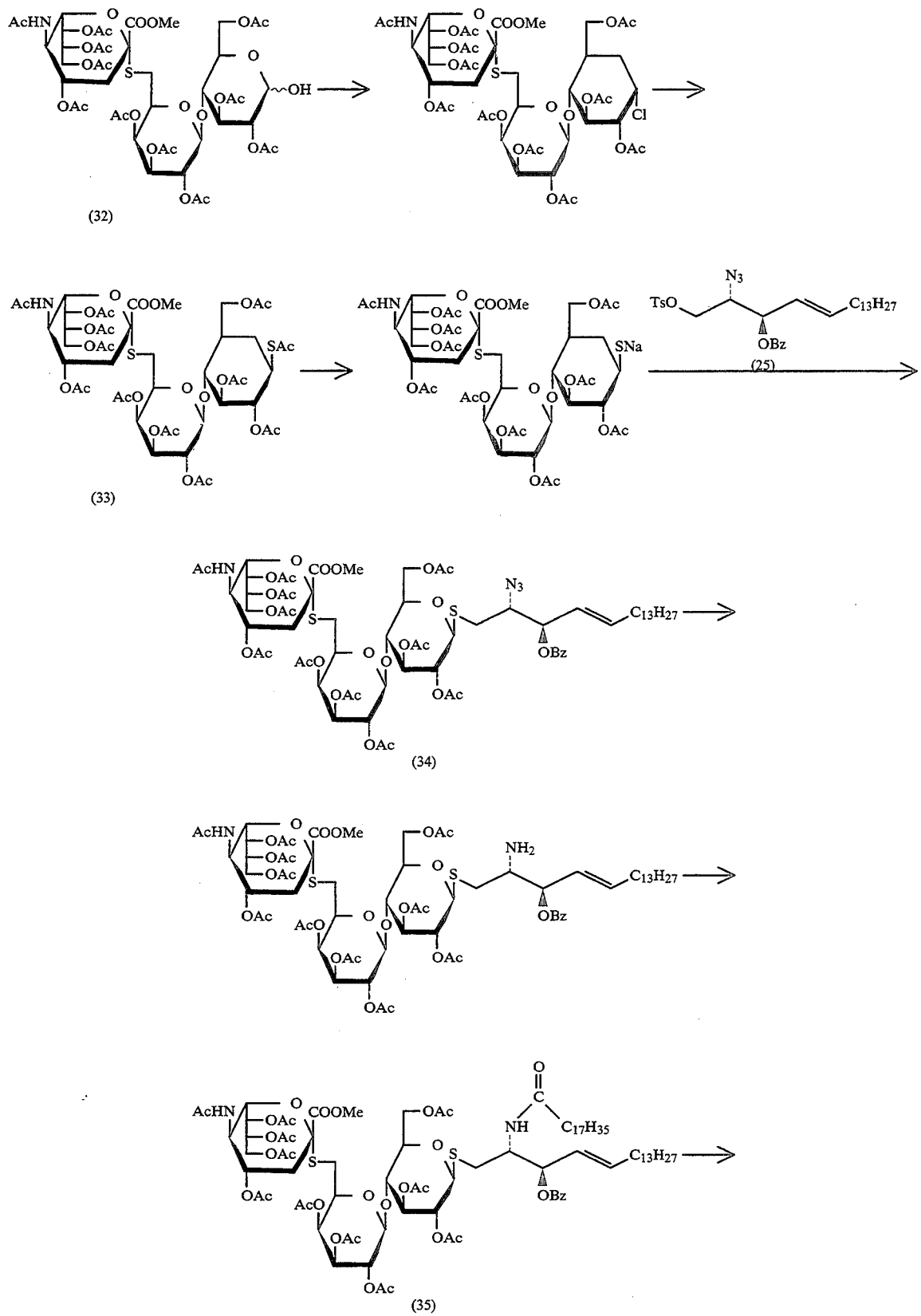

-continued
Scheme 4
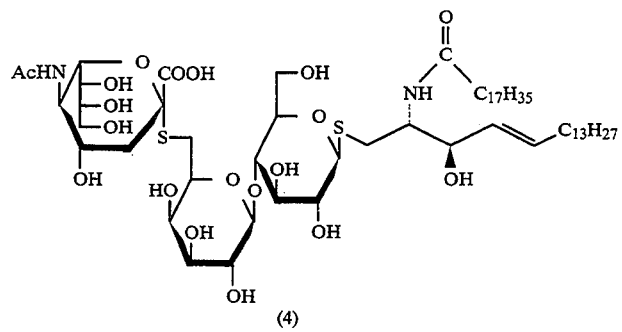
(4)
Scheme 5
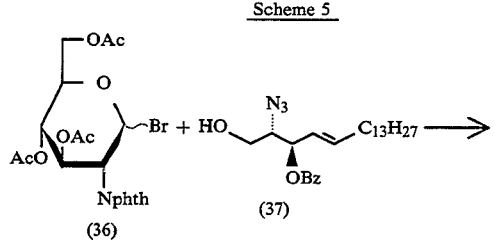
(36) + (37)
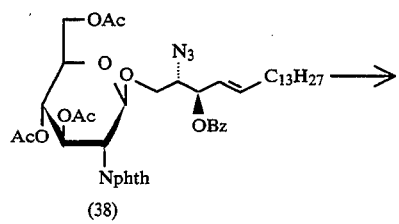
(38)
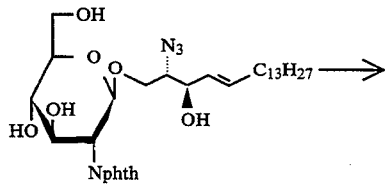
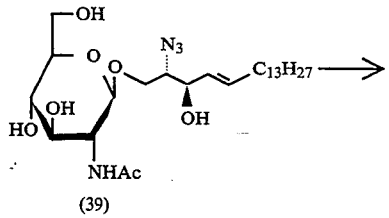
(39)
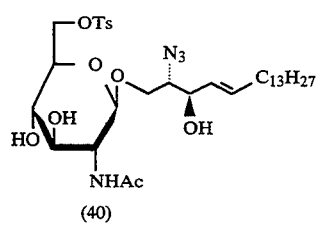
(40)
-continued
Scheme 5
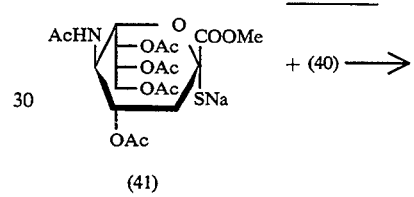
(41) + (40) →
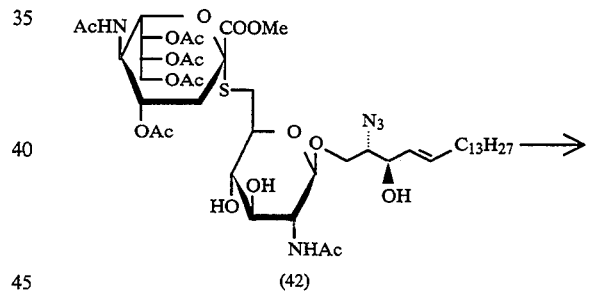
(42)
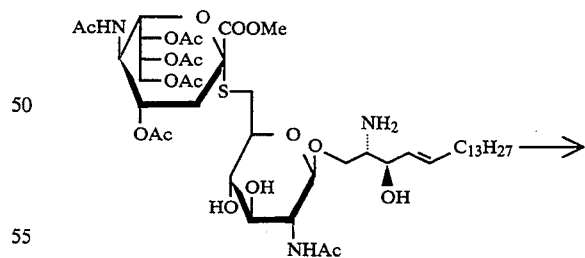
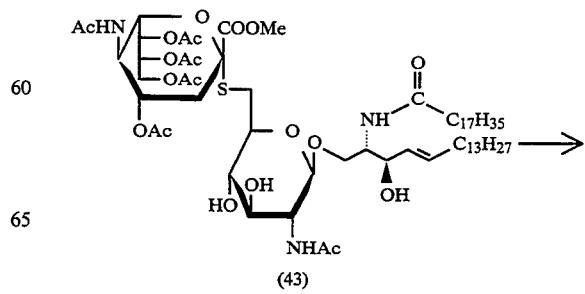
(43)

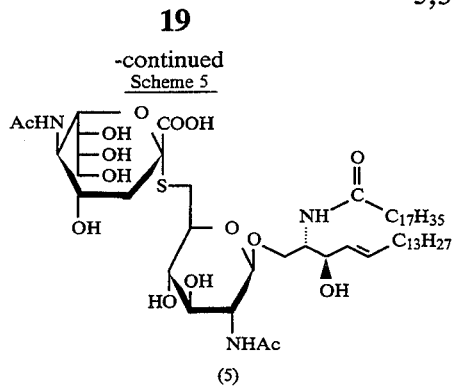

(5)

The invention is further Illustrated by the following examples.

EXAMPLE 1
Methyl(methyl 5-acetamido-3,5-dideoxy-8,9-O-isopropylidene-2-thio-D-glycero-α-D-galacto-2-nonulopyranosid)onate (Compound 8)

To a solution of methyl(methyl 5-acetamido-3,5-dideoxy-2-thio-D-glycero-α-D-galacto-2-nonulopyranosid)onate (Compound 7) (500 mg) dissolved in N,N-dimethylformamide (DMF, 5 ml) were added 2,2-dimethoxypropane (0.87 ml) and Drierite ® (calcium sulfate, anhydrous, Aldrich Chemical Co.) (1 g) and the mixture was stirred at room temperature for 2 hrs. After cooling to 0° C., a catalytic amount of p-toluenesulfonic acid monohydrate was added and the mixture was stirred for 1 hr. After a completion of the reaction was confirmed by thin layer chromatography (dichloromethane:methanol=10:1), the reaction solution was neutralized with NaHCO$_3$, filtered through Celite (filter agent, Wako Junyaku Co., Japan) and washed with methanol. The filtrate and washings were combined and concentrated under reduced pressure. The resulting syrup was subjected to column chromatography (Wakogel C-200) using 40/1 dichloromethane/methanol as an eluting solvent to afford. Compound 8 (390 mg, 70.1%).

$C_{16}H_{27}NO_8S$ 393.45

$[\alpha]_D = +12.06°$ (c=0.58, chloroform)

IR$\nu^{Film}_{max}$cm$^{-1}$ 3400 (NH), 1750 (ester), 1660, 1550 (amide), 860 [C(CH$_3$)$_2$]

270 MHz $^1$H-NMR(CD$_3$OD)δppm: 4.25 (q, 1H, $J_{7,8}=J_{8,9}=J_{8,9'}$6.4 Hz, H-8), 4.07(dd, 1H, $J_{9,9'}$8.2 Hz, H-9), 3.97(dd, 1H, H-9'), 3.79(s, 3H, Meo), 3.64(ddd, 1H, $J_{3e,4}$4.6 Hz, $J_{3a,4}$10.1 Hz, $J_{4,5}$10.1 Hz, H-4), 3.56(dd, 1H, $J_{6,7}$ 1.3 Hz, H-7), 3.38(dd, 1H, $J_{5,6}$ 10.4 Hz, H-6), 2.72(dd, 1H, $J_{3a,3e}$ 12.6 Hz, H-3e), 2.16, 1.98(2s, 6H, SMe and NAc), 1.72(t, 1H, H-3a), 1.36, 1.34(2s, 6H, CMe$_2$)

Methyl(methyl 5-acetamido-4,7-di-O-acetyl-3,5-dideoxy-8,9-isopropylidene-2-thio-D-glycero-α-D-galacto-2-nonulopyranosid)onate (Compound 9)

To a solution of Compound 8 (390 mg) dissolved in pyridine (4 ml ) was added acetic anhydride (2 ml) and the mixture was stirred overnight. After a completion of the reaction was confirmed by thin layer chromatography (dichloromethane:methanol=15:1), the mixture cooled to 0° C. was mixed with methanol and concentrated under reduced pressure. The resultant syrup was extracted with dichloromethane. The organic layer was washed with successive HCl and Na$_2$CO$_3$ and dehydrated with anhydrous Na$_2$SO$_4$. It was separated by filtration and washed with dichloromethane. The filtrate and washings were combined and concentrated under reduced pressure. The resultant syrup was subjected to column chromatography (Wakogel C-200) using 60/1 dichloromethane/methanol as an eluting solvent to afford Compound 9 (470 mg, quantitative).

$C_{20}H_{31}NO_{10}S$ 477.53

$[\alpha]_D = +14.56°$ (c=0.81, chloroform)

IR$\nu^{Film}_{max}$cm$^{-1}$ 3600–3200 (NH), 1750 (ester), 1670, 1550 (amide), 860 [C(CH$_3$)$_2$]

270 MHz $^1$H-NMR δppm: 5.45(d, 1H, $J_{NH,5}$ 9.9 Hz, NH), 5.39(dd, 1H, $J_{6,7}$ 2.0 Hz, $J_{7,8}$ 3.9 Hz, H-7), 4.96(ddd, 1H, $J_{3e,4}$ 4.8 Hz, $J_{3a,4}$ 11.8 Hz, $J_{4,5}$ 10.4 Hz, H-4), 4.62(ddd, 1H, $J_{8,9}$ 7.0 Hz, $J_{8,9'}$6.8 Hz, H-8), 3.85(s, 3H, MeO), 3.73(dd, 1H, $J_{5,6}$ 10.6 Hz, H-6), 2.78(dd, 1H, $J_{3a,3e}$ 12.8 Hz, H-3e), 2.17, 2.15, 2.03, 1.88(4s, 12H, SMe, 2O Ac and NAc), 1.36, 1.34(2s, 6H, C(C H$_3$)$_2$)

Methyl(methyl 5-acetamido-4,7-di-O-acetyl-3,5-dideoxy-2-thio-D-glycero-α-D-galacto-2-nonulopyranosid)onate (Compound 10)

Compound 9 (2.12 g) was dissolved in 80% aqueous acetic acid solution (20 ml) and the mixture was allowed to stand at 45° C. for 3.5 hrs. After a completion of the reaction was confirmed by thin layer chromatography (dichloromethane:methanol=10:1), the reaction solution was concentrated under reduced pressure. The resultant syrup was subjected to column chromatography (Wakogel C-200) using 80/1 dichloromethane/methanol as an eluting solvent to afford Compound 10 (1.73 g, 89.1%).

$C_{17}H_{27}NO_{10}S$ 437.46

$[\alpha]_D = +33.80°$ (c=0.704, chloroform)

IR$\nu^{Film}_{max}$cm$^{-1}$ 3700–3200 (OH, NH), 3000–2900 (CH), 1740 (ester), 1670, 1560 (amide)

270 MHz $^1$H-NMR(CDCl$_3$)δppm: 6.06(d, 1H, $J_{NH,5}$ 8.4 Hz, NH), 5.08(dd, 1H, $J_{6,7}$ 2.2 Hz, $J_{7,8}$ 9.3 Hz, H-7), 4.87(ddd, 1H, $J_{3e,4}$ 4.8 Hz, $J_{3a,4}$ 11.4 Hz, $J_{4,5}$ 10.4 Hz, H-4), 4.24(q, 1H, $J_{5,6}$ 10.3 Hz, H-5), 3.77(dd, 1H, H-6), 3.70 (s, 3H, MeO), 3.49(dd, 1H, $J_{5,9}$ 3.7 Hz, $J_{9,9'}$12.6 Hz, H-9).

Methyl (methyl 5-acetamido-4,7-di-O-acetyl-9-bromo-3,5,9-trideoxy-2-thio-D-glycero-α-D-galacto-2-nonulopyranosid)onate (Compound 11)

Compound 10 (2 g) was dissolved in pyridine (40 ml) and carbon tetrabromide (3.03 g) was added. After cooling the mixture to 0° C., triphenylphosphine (2.40 g) was added and the mixture was stirred at room temperature for 5 hrs. After a completion of the reaction was confirmed by thin layer chromatography (dichloromethane:methanol=15:1), the reaction solution was mixed with methanol and concentrated under reduced pressure. The resultant syrup was subjected to column chromatography (Wakogel C-200) using 2/1 ethyl acetate/hexane as an eluting solvent to afford Compound 11 (1.65 g, 72.1%).

$C_{17}H_{26}NO_9BrS$ 500.36

$[\alpha]_D = +38.51°$ (c=0.94, chloroform)

IR$\nu^{Film}_{max}$cm$^{-1}$ 3500–3200 (OH, NH), 1740 (ester), 1660, 1580 (amide)

270 MHz $^1$H-NMR(CDCl$_3$)δppm: 5.59(d, 1H, $J_{NH,5}$ 10.3 Hz, NH), 5.09(dd, 1H, $J_{6,7}$ 2.4 Hz, $J_{7,8}$ 8.6 Hz, H-7), 4.86(ddd, 1H, $J_{3e,4}$ 4.9 Hz, $J_{3a,4}$ 11.5 Hz, $J_{4,5}$ 10.3 Hz, H-4), 4.15(m, 1H, H-5), 3.89(s, 3H, MeO), 3.79(dd, 1H, $J_{5,6}$ 10.6 Hz, H-6), 3.51(dd, 1H, $J_{8,9}$ 2.8 Hz, $J_{9,9'}$ 11.0 Hz, H-9), 3.33(dd, 1H, $J_{8,9'}$ 7.0 Hz, H-9'), 2.81(dd, 1H, $J_{3a,3e}$ 12.9 Hz, H-3e), 2.16, 2.15, 2.05, 1.89(4s, 12H, SMe, 2AcO and NAc)

Methyl(methyl 5-acetamido-4,7,8-tri-O-acetyl-9-bromo-3,5,9-trideoxy-D-glycero-α-D-galacto-2-nonulopyranosid)onate (Compound 12)

To a solution of Compound 11 (1.35 g) dissolved in pyridine (10 ml) was added acetic anhydride (5 ml) and the mixture was stirred at room temperature overnight. After a completion of the reaction was confirmed by thin layer chromatography (dichloromethane:methanol=20:1), the mixture was mixed with methanol and concentrated under reduced pressure. The resultant syrup was extracted with dichloromethane. The organic layer was washed with successive HCl and Na$_2$CO$_3$ and dehydrated with anhydrous Na$_2$SO$_4$. It was separated by filtration and washed with dichloromethane. The filtrate and washings were combined and concentrated under reduced pressure. The resultant syrup was subjected to column chromatography (Wakogel C-200) using 2/1 ethyl acetate/hexane as an eluting solvent to afford Compound 12 (1.48 g, quantitative).

C$_{19}$H$_{28}$NO$_{11}$BrS 542.40

$[\alpha]_D$= +27.95° (c=0.88, chloroform)

IR$\nu^{Film}_{max}$cm$^{-1}$ 3300 (NH), 1740 (ester), 1660, 1540 (amide)

270 MHz $^1$H-NMR(CDCl$_3$)δppm: 5.84(d, 1H, $J_{NH,5}$ 9.7 Hz, NH), 5.35(m, 2H, H-7,8), 4.92(ddd, 1H, $J_{3e,4}$ 4.8 Hz, $J_{3a,4}$ 11.7 Hz, $J_{4,5}$ 10.3 Hz, H-4), 3.90(dd, 1H, $J_{6,7}$ 1.8Hz, $J_{5,6}$ 10.6 Hz, H-6), 3.83(dd, 1H, $J_{8,9}$ 2.8 Hz, H-9), 3.80 (s, 3H, MeO), 3.38(dd, 1H, $J_{8,9'}$ 6.1 Hz, $J_{9,9'}$ 11.4 Hz, H-9'), 2,76(dd, 1H, $J_{3a,3e}$ 12.6 Hz, H-3e), 2.16, 2.16, 2.15, 2.03, 1.85(5s, 15H, SMe, 3AcO and NAc)

2-(Trimethylsilyl)ethyl O-(methyl 5-acetamido-4,7,8-tri-O-acetyl-9-bromo-3,5,9-trideoxy-D-glycero-α-D-galacto-2-nonulopyranosylonate)-(2→3-)-O-(6-O-benzoyl-β-D-galactopyranosyl)-(1→4)-2,6-di-O-benzoyl-β-D-glucopyranoside (Compound 14)

Compound 12 (1.15 g) and Compound 13 (800 mg) were dissolved in acetonitrile (10 ml) and Molecular Sieves 3A (2.5 g) was added. The mixture was stirred at room temperature for 10 hrs. To the mixture cooled to −25° C. was added dimethyl(methylthio)sulfonium triflate (DMTST) (2.94 g, 74.6%) and the mixture was stirred at −15° C. for 2 hrs. After a completion of the reaction was confirmed by thin layer chromatography (dichloromethane:methanol=30:1, double development), the reaction solution was filtered with Celite and washed with dichloromethane. The filtrate and washings were combined and extracted with dichloromethane. The organic layer was washed with successive Na$_2$CO$_3$ and H$_2$O and dehydrated with anhydrous Na$_2$SO$_4$. It was separated by filtration. The filtrate and washings were combined and concentrated under reduced pressure. The resultant syrup was subjected to column chromatography (Wakogel C-200) using 3/1 ethyl acetate/hexane as an eluting solvent to afford Compound 14 (490 mg, 37.0%).

C$_{56}$H$_{70}$NO$_{23}$BrSi 1249.15

$[\alpha]_D$= +9.04° (c=0.774, chloroform)

IR$\nu^{Film}_{max}$cm$^{-1}$ 3700-3200 (NH, OH), 3100-2900 (CH), 1730 (ester), 1670, 1540 (amide), 860, 840 (Me$_3$Si), 710 (phenyl 270 MHz $^1$H-NMR(CDCl$_3$+CD$_3$OD)δppm:

Lactose unit 7.30-8.08(m, 15H, 3 Ph), 5.27(dd, 1H, H-2), 5.05(dd, 1H, H-6), 4.66(d, 1H, $J_{1,2}$ 8.1 Hz, H-1), 4.60(d, 1H, $J_{1,2'}$ 7.7 Hz, H-1'), 4.46(dd, 1H, $J_{5,6}$ 6.9 Hz, $J_{6,6'}$ 12.0 Hz, H-6), 4.37(dd, 1H, $J_{5,6'}$ 8.8 Hz, H-6'), 3.59(ddd, 1H, Me$_3$SiCH$_2$CH$_2$O), 0.88(m, 2H, Me$_3$SiCH$_2$CH$_2$O), Neu 5Ac unit 5.40(m, 1H, H-8), 5.23(dd, 1H, $J_{6,7}$ 2.4 Hz, $J_{7,8}$ 8.1 Hz, H-7), 4.91(ddd, 1H, $J_{3e,4}$ 4.8 Hz, $J_{3a,4}$ 12.1 Hz, $J_{4,5}$ 10.1 Hz, H-4), 3.82(s, 3H, MeO), 2.69(dd, 1H, $J_{3a,3e}$ 13.0 Hz, H-3e), 2.16, 2.11, 2.03(3 s, 9H, 3 AcO), 1.88(s, 3H, NAc)

2-(Triethylsilyl)ethyl O-(methyl 5-acetamido-4,7,8-tri-O-acetyl-9-bromo-3,5,9-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 15)

To a solution of Compound 14 (540 mg) dissolved in pyridine (6 ml) was added acetic anhydride (3 ml) and the mixture was stirred at room temperature overnight. After a completion of the reaction was confirmed by thin layer chromatography (dichloromethane:methanol=20:1 ), the mixture was mixed with methanol and concentrated under reduced pressure. The resultant syrup was extracted with dichloromethane. The organic layer was washed with successive HCl and Na$_2$CO$_3$ and dehydrated with anhydrous Na$_2$SO$_4$. It was separated by filtration and washed with dichloromethane. The filtrate washings were combined and concentrated under reduced pressure. The resultant syrup was subjected to column chromatography (Wakogel C-200) using 2/1 ethyl acetate/hexane as an eluting solvent to afford Compound 15 (550 mg, 92.5%).

C$_{62}$H$_{76}$NO$_{26}$BrSi 13.75.27

$[\alpha]_D$= +5.03° (c=0.636, chloroform)

IR$\nu^{Film}_{max}$cm$^{-1}$ 3700-3200 (NH), 3000-2900 (CH), 1750 (ester), 1660, 1580 (amide), 860, 840 (Me$_3$Si), 710 (phenyl)

270 MHz $^1$H-NMR(CDCl$_3$+CD$_3$OD)δppm:

Lactose unit 7.40-8.07(m, 15H, 3 Ph), 5.45(t, 1H, H-3), 5.22(dd, 1H, $J_{1,2}$ 7.9 Hz, $J_{2,7}$ 9.5 Hz, H-2), 5.07(d, 1H, $J_{3',4'}$ 3.3 Hz, H-4'), 4.87(d, 1H, $J_{1',2'}$ 7.9 Hz, H-1'), 4.69(d, 1H, H-1), 4.59(dd, 1H, $J_{2',3'}$ 10.3 Hz, H-3'), 3.58(m, 1H, OCH$_2$CH$_2$Si), 0.87(m, 2H, OCH$_2$CH$_2$Si).

Neu 5 Ac unit 5.42(m, 1H, H-8), 5.34(dd, 1H, $J_{6,7}$ 2.8 Hz, $J_{7,8}$ 6.2 Hz, H-7), 5.07(m, 1H, H-4), 3.77(s, 3H, MeO), 3.63(dd, 1H, $J_{5,6}$ 10.8 Hz, H-6), 3.42(dd, 1H, $J_{8,9}$ 6.2 Hz, $J_{9,9'}$ 11.7 Hz, H-9), 2.59(dd, 1H, $J_{3e,4}$ 5.0 Hz, $J_{3a,3e}$ 12.6 Hz, H-3e), 1.83(s, 3H, NAc), 1.65(t, 1H, $J_{3a,4}$ 12.6 Hz, H-3a).

Others 2.22. 2.12, 2.09, 2.03, 2.00, 1.98(6 s, 18H, 6 AcO)

2-(Trimethylsilyl)ethyl S-(methyl 5-acetamido-4,7,8,9-tetra-O-acetyl-3,5-dideoxy-D-glycero-α-D-galacto-2-nonulopyranosylonate-(2→9)-O-(methyl 5-acetamido-4,7,8-tri-O-acetyl-3,5-dideoxy-9-thio-D-glycero-α-D-galacto-2-nonulopyranosylonate-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 17)

Compound 15 (400 mg) and the sodium salt of methyl 5-acetamido-4,7,8,9-tetra-O-acetyl-3,5-dideoxy-2-thio-D-glycero-α-D-galacto-2-nonulopyranosylonate (Compound 16) (308 g) were dissolved in N,N-dimethylformamide (5 ml) and the solution was stirred at room temperature overnight in a nitrogen stream. After a completion of the reaction was confirmed by thin layer chromatography (dichloromethane:methanol=20:1), the reaction solution was concentrated under reduced pressure. The resultant syrup was subjected to column chromatography (Wakogel C-200) using ethyl acetate as an eluting solvent to afford Compound 17 (421 mg, 80.3%).

$C_{82}H_{103}N_2O_{38}SSi$ 1801.86

$[\alpha]_D = +8.90°$ (c=0.584, chloroform)

IR$\nu^{Film}_{max}$cm$^{-1}$ 3700–3200 (NH), 3100–2900 (CH), 1740 (ester), 1670, 1550 (amide), 860, 840 (Me$_3$Si), 710 (phenyl)

270 MHz $^1$H-NMR(CDCl$_3$)δppm:

Lactose unit 7.39–8.90(m, 15H, 3 Ph), 5.46(t, 1H, J$_{3,4}$ 9.9 Hz, J$_{2,3}$ 9.7 Hz, H-3), 5.20(dd, 1H, J$_{1,2}$ 7.7 Hz, H-2), 5.04(d, 1H, H-4'), 4.86(d, 1H, J$_{1',2'}$8.1 Hz, H-1'), 4.66(d, 1H, H-1), 3.55(m, 1H, OCH$_2$CH$_2$Si), 0.90 (m, 2H, OCH$_2$CH$_2$Si).

Neu 5 Ac unit 5.34(m, 4H, H-7,8, 7',8'), 4.79(m, 2H, H-4,4'), 3.77, 3.71(2 s, 6H, 2 MeO), 2.81(m, 2H, H-9a,99b), 2.62(dd, 1H, J$_{3'e,4'}$4.2 Hz, J$_{3'a, 3'e}$ 12.5 Hz, H-3'e), 2.57(dd, 1H, J$_{3e,4}$ 4.2 Hz, J$_{3a,3e}$ 12.3 Hz, H-3e), 1.85(2s, 6H, 2NAc), 1.63(t, 1H, H-3a), Others 2.21, 2.21, 2.12, 2.10, 2.09, 2.06, 2.02, 2.02, 2.00, 2.00(10 s, 30H, 10 AcO)

S-(Methyl 5-acetamido-4,7,8,9-tetra-O-acetyl-3,5-dideoxy-D-glycero-α-D-galacto-2-nonulopyranosylonate)-(2→9)-O-(methyl 5-acetamido-4,7,8-tri-O-acetyl-3,5-dideoxy-9-thio-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranose (Compound 18)

Compound 17 (300 mg) was dissolved in acetonitrile (2 ml). To the cooled solution to 0° C. was added boron trifluoride diethyl ether (0.2 ml) and the mixture was stirred at 0° C. for 2.5 hrs. After a completion of the reaction was confirmed by thin layer chromatography (dichloromethane:methanol=15:1), the reaction solution was extracted with dichloromethane. The organic layer was washed with successive Na$_2$CO$_3$ and H$_2$O and dehydrated with anhydrous Na$_2$SO$_4$. It was separated by filtration and washed with dichloromethane. The filtrate washings were combined and concentrated under reduced pressure. The resultant syrup was subjected to column chromatography (Wakogel C-200) using 40/1 dichloromethane/methanol as an eluting solvent to afford Compound 18 (260 mg, 91.8%).

$C_{77}H_{92}N_2O_{38}S$ 1701.63

$[\alpha]_D = +28.78°$ (c=0.66, chloroform)

IR$\nu^{Film}_{max}$cm$^{-1}$ 3700–3200 (NH, OH), 3100–2900 (CH, 1740 (ester), 1660, 1540 (amide), 710 (phenyl)

270 MHz $^1$H-NMR(CDCl$_3$)δppm:

Lactose unit 7.39–8.08(m, 15H, 3 Ph), 5.79(t, 1H, J$_{2,3}$=J$_{3,4}$=9.7 Hz, H-3), 5.04(d, 1H, H-4'), 4.96(d, 1H, J$_{1',2'}$7.7 Hz, H-1'), 4.66(dd, 1H, J$_{3',4'}$3.3 Hz, J$_{2',3'}$10.1 Hz, H-3').

Neu 5 Ac unit 5.30–5.35(m, 4H, H-7,8,7',8'), 4.80(m, 2H, H-4,4'), 3.76, 3.74(2 s, 6H, 2 MeO), 2.82(m, 2H, H-9a,9b), 2.62(m, 1H, H-3e), 2.57(dd, 1H, J$_{3e,4}$ 4.4 Hz, J$_{3a,3e}$ 12.6 Hz, H-3e), 1.85, 1.84(2 s, 6H, 2 NAc).

Others 2.20, 2.19, 2.14, 2.06, 2.04, 2.03, 2.03, 2.01, 1.99, 1.99(10 s, 30H, 10 AcO)

S-(Methyl 5-acetamido-4,7,8,9-tetra-O-acetyl-3,5-dideoxy-D-glycero-60-D-galacto-2-nonulopyranosylonate)-(2→9)-O-(methyl 5-acetamido-4,7,8-tri-O-acetyl-3,5-dideoxy-9-thio-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-galactopyranosyltrichloracetimidate (Compound 19)

Compound 18 (200 mg) was dissolved in dichloromethane (2 ml) and trichloroacetonitrile (0.12 ml) was added. After cooling the mixture to 0° C., 1,8-diazabicyclo[5.4.0]-7-undecene (DBU, 0.018 ml) was added and the mixture was stirred at 0° C. for 2 hrs. After a completion of the reaction was confirmed by thin layer chromatography (dichloromethane:methanol=15:1), the reaction solution was subjected to column chromatography (Wakogel C-200) using 30/1 dichloromethane/methanol as an eluting solvent to afford Compound 19 (216 mg, quantitative).

$C_{79}H_{92}N_3O_{38}SCl_3$ 1846.01

$[\alpha]_D = +29.34°$ (c=0.518, chloroform)

IR$\nu^{Film}_{max}$cm$^{-1}$ 3700–3200 (NH), 3100–2900 (CH), 1740 (ester), 1670, 1540 (amide), 710 (phenyl)

270 MHz $^1$H-NMR(CDCl$_3$)δppm:

Lactose unit 8.56(s, 1H, C=NH), 7.38–8.09(m, 15H, 3 Ph), 6.65(d, 1H, J$_{1,2}$ 4.0 Hz, H-1), 5.83(t, 1H, J$_{2,3}$=J$_{3,4}$=9.7 Hz, H-3), 5.06(d, 1H, H-4'), 4.93(d, 1H, J$_{1',2'}$8.1 Hz, H-1'), 4.66(dd, 1H, J$_{3',4'}$3.3 Hz, J$_{2',3'}$10.1 Hz, H-3'), Neu 5 Ac unit 5.63(d, 1H, J$_{NH,5}$ 9.9 Hz, NH), 5.36(m, 4H, H-7,8,7',8'), 4.84(m, 2H, H-4,4'), 3.78, 3.75(2 s, 6H, 2 MeO), 2.83(m, 2H, H-9a, 9b), 2.63(dd, 1H, J$_{3'a,4'}$4.6 Hz, J$_{3'a,3'c}$ 12.5 Hz, H-3'e), 2.58(dd, 1H, J$_{3c,4}$ 4.4 Hz, J$_{3a,3c}$ 12.5 Hz, H-3e), 1.87, 1.87(2 s, 6H, 2 NAc), 1.65(t, 1H, H-3a).

Others 2.22, 2.18, 2.14, 2.08, 2.08, 2.05, 2.04, 2.03, 2.00, 2.00(10 s, 30H, 10 AcO)

S-(Methyl 5-acetamido-4,7,8,9-tetra-O-acetyl-3,5-dideoxy-D-glycero-α-D-galacto-2-nonulopyranosylonate)-(2→9)-O-(methyl 5-acetamido-4,7,8-tri-O-acetyl-3,5-dideoxy-9-thio-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-benzoyloxy-4-octadecene-1,3-diol (Compound 21)

Compound 19 (247 mg) and (2S,3R,4E)-2-azido-3-benzoyloxy-4-octadecene-1,3-diol (Compound 20) (172 mg) were dissolved in dichloromethane (6 ml) and Molecular Sieves 4-A type AW-300 (2 g) was added. The mixture was stirred at room temperature for 1.5 hrs. After cooling it to −15° C., boron trifluoride diethyl ether (0.02 ml ) was added and the mixture was stirred at −15° C. for 4 hrs. After a completion of the reaction was confirmed by thin layer chromatography (dichloromethane:methanol=15:1), the reaction solution was filtered through Celite to separate the solid matter by filtration, which was washed with dichloromethane. The combined filtrate and washings were extracted with dichloromethane. The organic layer was washed with successive Na$_2$CO$_3$ and H$_2$O and dehydrated with anhydrous Na$_2$SO$_4$. It was separated by filtration and washed with dichloromethane. The combined filtrate and washings were concentrated under reduced pressure. The resultant syrup was subjected to column chromatography (Wakogel C-200) using 40/1 dichloromethane/methanol as an eluting solvent to afford Compound 21 (210 mg, 74.3%).

$C_{102}H_{129}N_5O_{40}S$ 2113.21

$[\alpha]_D = +1.64°$ (c=0.608, chloroform)

IR$\nu^{Film}_{max}$cm$^{-1}$  3700–3200 (NH), 3000–2900 (CH), 2100 (N$_3$), 1740 (ester), 1670, 1540 (amide), 710 (phenyl)

270 MHz $^1$H-NMR(CDCl$_3$)δppm:

Lactose unit 5.44(t, 1H, H-3), 5.23(dd, 1H, $J_{2,3}$ 9.5 Hz, H-2), 5.05(d, 1H, H-4′), 5.00(t, 1H, H-2′), 4.85(d, 1H, $J_{1,2}$ 7.9 Hz, H-1), 4.67(d, 1H, $J_{1′,2′}$ 7.5 Hz, H-1′), 4.64(dd, 1H, $J_{2′,3′}$ 10.3 Hz, $J_{3′,4′}$ 2.9 Hz, H-3′).

Neu 5 Ac unit 5.62(d, 1H, $J_{NH,5}$ 8.1 Hz, NH), 5.36(m, 4H, H-7,8,7′,8′), 5.17(d, 1H, $J_{NH,5}$ 10.3 Hz, NH), 4.82(m, 2H, H-4,4′), 3.78, 3.74(2 s, 6H, 2 MeO), 2.82(m, 2H, H-9a,9b), 2.64(dd, 1H, $J_{3′e,4′}$ 4.4 Hz, $J_{3′a,3′e}$ 12.8 Hz, H-3′e), 2.58(dd, 1H, $J_{3e,4}$ 4.4 Hz, $J_{3a,3e}$ 12.6 Hz, H-3e), 1.87, 1.87(2 s, 6H, 2 NAc), 1.65(t, 1H, H-3a).

Sphingosine unit 5.65(dt, 1H, $J_{4,5}$ 15.4 Hz, $J_{5,6} = J_{5,6′}$ 6.8 Hz, H-5), 5.51(dd, 1H, $J_{2,3}$ 3.7 Hz, $J_{3,4}$ 8.1 Hz, H-3), 5.40(dd, 1H, H-4), 1.25(s, 22H, 11CH$_2$), 0.88(t, 3H, CH$_3$).

Others 7.32–8.09(m, 20H, 4 Ph), 2.23, 2.17, 2.12, 2.10, 2.07, 2.05, 2.02, 2.01, 2.00, 1.99(10 s, 30H, 10 AcO)

S-(Methyl 5-acetamido-4,7,8,9-tetra-O-acetyl-3,5-dideoxy-D-glycero-α-D-galacto-2-nonulopyranosylonate)-(2→9)-O-(methyl 5-acetamido-4,7,8-tri-O-acetyl-3,5-dideoxy-9-thio-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-benzoyloxy-2-octadecanamide-4-octadecene-1,3-diol (Compound 22)

Compound 21 (180 mg) was dissolved in pyridine (10 ml) and water (2 ml). After cooling to 0° C., the solution was stirred at 0° C. to w.t. for 3 days while blowing hydrogen sulfide. After a completion of the reaction was confirmed by thin layer chromatography (dichloromethane:methanol=15:1), the reaction solution was concentrated at 30° C. under reduced pressure. The resultant syrup was dissolved in dichloromethane (8 ml), 1-ethyl-3-(3-dimethylaminopropyl)carbodiimide hydrochloride (WSC, 49 mg) and stearic acid (73 mg) were added and the mixture was stirred at room temperature overnight. After a completion of the reaction was confirmed by thin layer chromatography (dichloromethane:methanol=15:1), the reaction solution was extracted with dichloromethane. The organic layer was washed with water and dehydrated with anhydrous Na$_2$SO$_4$. It was separated by filtration. The combined filtrate and washings were concentrated under reduced pressure. The resultant syrup was subjected to column chromatography (Wakogel C-200) using 50/1 dichloromethane/methanol as an eluting solvent to afford Compound 22 (193 mg, 96.3%).

$C_{102}H_{165}N_3O_{41}S$ 2353.68

$[\alpha]_D = +12.81°$ (c=0.64, chloroform)

IR$\nu^{Film}_{max}$cm$^{-1}$ 3700–3200 (NH), 2950, 2850 (CH), 1740 (ester), 1660, 1540 (amide), 710 (phenyl)

270 MHz $^1$H-NMR(CDCl$_3$)δppm:

Lactose unit 5.17(t, 1H, H-2), 5.05(d, 1H, H-4′), 5.02(dd, 1H, $J_{2,3}$ 9.9 Hz, H-2), 4.83(d, 1H, $J_{1′,2′}$ 8.1 Hz, H-1′), 4.65(dd, 1H, $J_{3′,4′}$ 2.7 Hz, $J_{2′,3′}$ 9.7 Hz, H-3′), 4.60(d, 1H, $J_{1,2}$ 7.5 Hz, H-1).

Neu 5 Ac unit 5.37(m, 4H, H-7,8,7′,8′), 5.19(d, 1H, $J_{NH,5}$ 9.9 Hz, NH), 4.87(m, 2H, H-4,4′), 3.77, 3.75(2 s, 6H, 2 MeO), 2.90(dd, 1H, H-9a), 2.80(dd, 1H, $J_{8,9b}$ 9.3 Hz, $J_{9a,9b}$ 13.6 Hz, H-9b), 2.65(dd, 1H, $J_{3′c,4′}$ 4.6 Hz, $J_{3′a,3′c}$ 12.6 Hz, H-3′e), 2.57(dd, 1H, $J_{3e,4}$ 4.4 Hz, $J_{3a,3c}$ 12.8 Hz, H-3e), 1.87, 1.75(2 s, 6H, 2 NAc), 1.64(t, 1H, H-3a).

Ceramide unit 5.76(dt, 1H, $J_{4,5}$ 14.7 Hz, $J_{5,6} = J_{5,6′}$ 7.0 Hz, H-5), 1.26(s, 50H, 25CH$_2$), 0.88(t, 6H, 2CH$_3$).

Others 7.24–8.09(m, 20H, 5 Ph), 2.23, 2.14, 2.12, 2.11, 2.08, 2.06, 2.01, 2.00, 2.00, 1.87(10 s, 30H, 10 AcO)

S-(5-Acetamido-3,5-dideoxy-D-glycero-α-D-galacto-2-nonulopyranosylonic acid)-(2→9)-O-(5-acetamido-3,5-dideoxy-9-thio-D-glycero-α-D-galacto-2-nonulopyranosylonic acid)-(2→3)-O-β-D-galactopyranosyl)-(1→4)-O-β-D-glucopyranosyl-(1→1)-(2S,3R,4E)-2-octadecanamid-4-octadecene-1,3-diol (Compound 1)

Compound 22 (130 mg) was dissolved in methanol (4 ml) and a catalytic amount of 28% sodium methylate was added, and the mixture was stirred at room temperature overnight. After a completion of the reaction was confirmed by thin layer chromatography (butanol:methanol:water=4:2:1), the reaction solution was mixed with 0.2N KOH aqueous solution (2 ml) and further stirred one day. After a completion of the reaction was confirmed by thin layer chromatography (butanol:methanol:water=4:2:1), the reaction solution was neutralized with an ion-exchange resin, Amberlite IR-120(H$^+$) 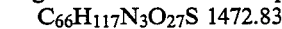 and separated by filtration, and washed with a mixed solvent of 10/10/1 chloroform/methanol/water. The combined filtrate and washings were concentrated under reduced pressure. The resultant syrup was subjected to column chromatography (Sephadex LH-20) using 10/10/1 chloroform/methanol/water as an eluting solvent to afford Compound 1 (81 mg, quantitative).

$C_{66}H_{117}N_3O_{27}S$ 1472.83

$[\alpha]_D = +24.48°$ (c=0.49, chloroform:methanol=1:1)

270 MHz $^1$H-NMR(d$_6$-DMSO: D$_2$O=49:1)δppm:

Neu 5 Ac unit 2.75, 2.68(2 m, 2H, H-3e, 3e′), 1.89, 1.66(2 s, 6H, 2 NAc).

Lactose unit 4.43(d, 1H, $J_{1′,2′}$ 6.2 Hz, H-1′), 4.17(d, 1H, $J_{1,2}$ 7.2 Hz, H-1).

Ceramide unit 5.54(dt, 1H, H-5), 5.34(dd, 1H, $J_{3,4}$ 5.9 Hz, $J_{4,5}$ 15.4 Hz, H-4), 2.04(t, 2H, $J_{CH2CH2CO}$ 6.6 Hz, CH$_2$CH$_2$CO), 1.24(s, 50H, 25CH$_2$), 0.85(t, 6H, 2CH$_3$)

EXAMPLE 2

S-(Methyl 5-acetamido-4,7,8,9-tetra-O-acetyl-3,5-dideoxy-D-glycero-α-D-galacto-2-nonulopyranosylonate)-(2→6)-2,3,4-tri-O-acetyl-1-S-acetyl-1,6-dithio-β-D-glucopyranose (Compound 24)

S-(Methyl 5-acetamido-4,7,8,9-tetra-O-acetyl-3,5-dideoxy-D-glycero-α-D-galacto-2-nonulopyranosylonate)-(2→6)-2,3,4-tri-O-acetyl-6-thio-D-glucopyranose (Compound 23) (500 mg) was dissolved in dichloromethane (5 ml) and 2,4,6-collidine (0.5 ml) was added. The mixture was cooled to −15° C. and methanesulfonylchloride (0.25 ml) was added. The mixture was stirred at −15° C. for 20 minutes and further stirred at room temperature for 1 hr. After a completion of the reaction was confirmed by thin layer chromatography (dichloromethane:methanol=15:1), 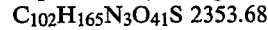

the reaction solution was extracted with dichloromethane. The organic layer was washed with successive HCl and H$_2$O and dehydrated with anhydrous Na$_2$SO$_4$. It was separated by filtration and washed with dichloromethane. The combined filtrate and washings were concentrated under reduced pressure. The resultant syrup was dissolved in acetone (7 ml), mixed with Drierite ®(1 g) and stirred for 2 hrs. Potassium thioacetate (430 mg) was added and the mixture was stirred at 45° C. overnight. After a completion of the reaction was confirmed by thin layer chromatography (dichloromethane:methanol=15:1), the reaction solution was filtered through Celite and washed with dichloromethane. The combined filtrate and washings were concentrated under reduced pressure. The resultant syrup was subjected to silica gel column chromatography (Wakogel C-200) using 120/1 dichloromethane/methanol as an eluting solvent to afford Compound 24 (310 mg, 57.8%).

C$_{34}$H$_{47}$NO$_{20}$S$_2$ 853.86

$[\alpha]_D = +38.00°$ (c=0.8, chloroform)

IR$\nu^{Film}_{max}$cm$^{-1}$ 3700–3200 (NH), 3100–2900 (CH), 1750 (ester), 1670, 1540 (amide)

270 MHz $^1$H-NMR(CDCl$_3$)δppm:

Glucose unit 5.22(d, 1H, J$_{1,2}$ 10.3 Hz, H-1), 5.07(t, 1H, J$_{2,3}$ 9.3 Hz, H-2), 4.96(t, 1H, J$_{3,4}$ 9.5 Hz, H-3), 2.88(m, 2H, H-6,6'), 2.38(s, 3H, SAc).

Neu 5 Ac unit 5.30(m, 2H, H-7,8), 4.87(m, 1H, H-4), 4.28(dd, 1H, J$_{9,9'}$12.8 Hz, H-9), 3.82(s, 3H, MeO), 2.71(dd, 1H, J$_{3e,4}$ 4.2 Hz, J$_{3a,3e}$ 12.5 Hz, H-3e), 1.87(s, 3H, NAc).

Others 2.14, 2.13, 2.09, 2.05, 2.03, 2.01, 2.00(7 s, 21H, 7 AcO)

S-(Methyl 5-acetamido-4,7,8,9-tetra-O-acetyl-3,5-dideoxy-D-glycero-α-D-galacto-2-nonulopyranosylonate)-(2→6)-S-(2,3,4-tri-O-acetyl-6-thio-β-D-glucopyranosyl)-(1→1)-(2R,3R,4E)-2-azido-3-benzoyloxy-4-octadecene-1-thiol (Compound 26)

Compound 24 (300 mg) was dissolved in methanol (2 ml) and the solution was cooled to −30° C. Methanol (0.3 ml) containing Na (8 mg) was added dropwise and the mixture was stirred at −30° C. for 5 minutes. After a completion of the reaction was confirmed by t.l.c. (ethyl acetate), the reaction solution was concentrated at a water temperature under reduced pressure. The resultant syrup and (2S,3R,4E)-2-azido-3-benzoyloxy-1-O-(p-toluenesulfonyl)-4-octadecene-1,3-diol (Compound 25) (410 mg) were dissolved in N,N-dimethylformamide (4.5 ml) and stirred at 45° C. overnight in a nitrogen stream. Pyridine (4 ml) and acetic anhydride (2 ml) were added and the mixture was stirred at room temperature one day. After a completion of the reaction was confirmed by thin layer chromatography (dichloromethane:methanol=15:1), the reaction solution was concentrated under reduced pressure. The resultant syrup was subjected to silica gel column chromatography (Wakogel C-200) using 100/1 dichloromethane/methanol as an eluting solvent to afford Compound 26 (165 mg, 38.4%).

C$_{57}$H$_{82}$N$_4$O$_{11}$S$_2$ 1223.41

$[\alpha]_D = -6.34°$ (c=0.946, chloroform)

IR$\nu^{Film}_{max}$cm$^{-1}$ 3700–3200 (NH), 2950, 2850 (CH), 2100 (N$_3$), 1750 (ester), 1670, 1540 (amide) 710 (phenyl)

270 MHz $^1$H-NMR(CDCl$_3$)δppm:

Glucose unit 5.24(dd, 1H, H-4), 5.01(t, 1H, J$_{2,3}$ 9.3 Hz, H-2), 4.98(t, 1H, J$_{3,4}$ 9.5 Hz, H-3), 4.59(d, 1H, J$_{1,2}$ 10.1 Hz, H-1), 2.85–2.92(m, 2H, H-6,6').

Neu 5 Ac unit 5.29(m, 2H, H-7,8), 4.83(ddd, 1H, J$_{3e,4}$ 4.6 Hz, J$_{3a,4}$ 11.2 Hz, J$_{4,5}$ 10.6 Hz, H-4), 4.27(dd, 1H, H-9), 4.10(dd, 1H, H-9'), 3.75(s, 3H, MeO), 2.60(dd, 1H, J$_{3a,3e}$ 13.0 Hz, H-3e), 1.87(s, 3H, NAc), 7.44–8.10(m, 5H, Ph).

Sphingosine unit 5.97(dt, 1H, J$_{5,6}$=J$_{5,6'}$6.7 Hz, H-5), 5.68(dd, 1H, J$_{2,3}$ 3.3 Hz, J$_{3,4}$ 8.1 Hz, H-3), 5.55(dd, 1H, J$_{4,5}$ 15.4 Hz, H-4), 2.85–2.92(m, 1H, H-1), 2.63(dd, 1H, J$_{1',2'}$8.8 Hz, J$_{1,1'}$14.5 Hz, H-1'), 1.24(s, 22H, 11CH$_2$), 0.88(t, 3H, CH$_3$).

Others 2.12, 2.12, 2.10, 2.05, 2.04, 2.03, 2.00(7 s, 21H, 7 AcO)

S-(Methyl 5-acetamido-4,7,8,9-tetra-O-acetyl-3,5-dideoxy-D-glycero-α-D-galacto-2-nonulopyranosylonate)-(2→6)-S-(2,3,4-tri-O-acetyl-6-thio-β-D-glucopyranosyl)-(1→1)-(2R,3R,4E)-3-benzyloxy-2-octadecanamid-4-octadecene-1-thiol (Compound 27)

Compound 26 (165 mg) was dissolved in pyridine (10 ml) and water (2 ml). After cooling to 0° C., the solution was stirred at 0° C. to w.t. for 3 days while blowing hydrogen sulfide. After a completion of the reaction was confirmed by thin layer chromatography (dichloromethane:methanol=15:1), the reaction solution was concentrated at 30° C. under reduced pressure. The resultant syrup was dissolved in dichloromethane (10 ml), 1-ethyl-3-(3-dimethylaminopropyl)carbodiimide hydrochloride (WSC, 78 mg) and stearic acid (115 mg) were added and the mixture was stirred at room temperature for 3 hrs. After a completion of the reaction was confirmed by thin layer chromatography (dichloromethane:methanol=15:1), the reaction solution was extracted with dichloromethane. The organic layer was washed with water and dehydrated with anhydrous Na$_2$SO$_4$. It was separated by filtration and washed with dichloromethane. The combined filtrate and washings were concentrated under reduced pressure. The resultant syrup was subjected to silica gel column chromatography (Wakogel C-200) using 110/1 dichloromethane/methanol as an eluting solvent to afford Compound 27 (160 mg, 81%).

C$_{75}$H$_{118}$N$_2$O$_{22}$S$_2$ 1463.88

$[\alpha]_D = +14.66°$ (c=0.6, chloroform)

IR$\nu^{Film}_{max}$cm$^{-1}$ 3600–3200 (NH), 2950, 2850 (CH), 1750 (ester), 1600, 1540 (amide), 710 (phenyl)

270 MHz $^1$H-NMR(CDCl$_3$)δppm:

Glucose unit 4.98(t, 1H, J$_{2,3}$ 9.7 Hz, H-2), 4.93(t, 1H, J$_{3,4}$ 9.4 Hz, H-3), 4.51(d, 1H, J$_{1,2}$ 9.9 Hz, H-1), 2.84–2.92(m, 2H, H-6,6').

Neu 5 Ac unit 5.29(m, 2H, H-7,8), 4.86(ddd, 1H, J$_{3e,4}$ 4.2 Hz, J$_{3a,4}$ 11.5 Hz, J$_{4,5}$ 11.0 Hz, H-4), 4.28(dd, 1H, H-9), 4.09(dd, 1H, J$_{8,9'}$4.6 Hz, J$_{9,9'}$13.6 Hz, H-9'), 3.79(s, 3H, MeO), 2.64(dd, 1H, J$_{3a,3e}$12.8 Hz, H-3e), 1.87(s, 3H, NAc).

Ceramide unit 7.43–8.07(m, 5H, Ph), 5.87(m, 1H, H-5), 5.85(d, 1H, J$_{NH,2}$ 8.8 Hz, NH), 5.57(t, 1H, J$_{3,4}$ 6.8 Hz, H-3), 5.49(dd, 1H, J$_{4,5}$ 15.4 Hz, H-4), 4.46(m, 1H, H-2), 3.08(dd, 1H, J$_{1,2}$ 3.7 Hz, J$_{1,1'}$13.0 Hz, H-1), 2.83(dd, 1H, J$_{1',2}$ 9.2 Hz, H-1'), 1.24(s, 50H, 25CH$_2$), 0.88(t, 6H, 2 CH$_3$).

Others 2.13, 2.12, 2.09, 2.04, 2.03, 2.00, 1.99(7 s, 21H, 7 AcO)

S-(5-Acetamido-3,5-dideoxy-D-glycero-α-D-galacto-2-nonulopyranosylonic acid)-(2→6)-S-(6-thio-β-D-glucopyranosyl-(1→1)-(2R,3R,4E)-3-hydroxy-2-octadecanamid-4-octadecene-1-thiol (Compound 2)

Compound 27 (100 mg) was dissolved in methanol 3 ml) and a catalytic amount of 28% sodium methylate was added, and the mixture was stirred at room temperature for 7 hrs. After a completion of the reaction was confirmed by thin layer chromatography (butanol:methanol:water=4:2:1), the reaction solution was mixed with 0.2N KOH aqueous solution (2 ml) and further stirred overnight. After a completion of the reaction was confirmed by thin layer chromatography (butanol:methanol:water=4:2:1), the reaction solution was neutralized with an ion-exchange resin, Amberlite IR-120(H+) and separated by filtration, and washed with a mixed solvent of 10/10/1 chloroform/methanol/water. The combined filtrate and washings were concentrated under reduced pressure. The resultant syrup was subjected to column chromatography (Sephadex LH-20) using 10/10/1 chloroform/methanol/water as an eluting solvent to afford Compound 2 (68 mg, 94.7% ).

$C_{53}H_{98}N_2O_{14}S_2$ 1051.49

$[\alpha]_D = +15.90°$ (c=0.44, chloroform)

IR$\nu^{KBr}_{max}$cm$^{-1}$

270 MHz $^1$H-NMR(d$_6$-DMSO: D$_2$O=49:1)δppm:

Neu 5 Ac unit 2.75(m, 1H, 3e), 1.88(s, 3H, NAc).

Glucose unit 4.20(d, 1H, $J_{1,2}$ 9.2 Hz, H-1), 2.91(dd, 1H, $J_{5,6}$ 2.9 Hz, $J_{6,6'}$13.2 Hz, H-6).

Ceramide unit 5.55(dt, 1H, $J_{5,6}=J_{5,6'}$6.6 Hz, $J_{4,5}$ 14.8 Hz, H-5), 5.35 (dd, 1H, $H_{3,4}$ 5.7 Hz, H-4), 2.04(t, 2H, CH$_2$CH$_2$CO), 1.24(s, 50H, 25CH$_2$), 0.85 (t, 6H, 2CH$_3$)

EXAMPLE 3

S-(Methyl 5-acetamido-4,7,8,9-tetra-O-acetyl-3,5-dideoxy-D-glycero-α-D-galacto-2-nonulopyranosylonate)-(2→6)-2,3,4-tri-O-acetyl-1-S-acetyl-1-thio-β-D-galactopyranose (Compound 29)

S-(Methyl 5-acetamido-4,7,8,9-tetra-O-acetyl-3,5-dideoxy-D-glycero-α-D-galacto-2-nonulopyranosylonate)-(2→6)-2,3,4-tri-O-acetyl-6-thio-D-galactopyranose (Compound 28) (1.44 g) was dissolved in dichloromethane (14 ml) and 2,4,6-collidine (1.4 ml) was added. The mixture was cooled to −15° C. and methanesulfonylchloride (0.7 ml) was added. The mixture was stirred at −15° C. for 30 minutes and further stirred at room temperature for 2 hrs. After a completion of the reaction was confirmed by thin layer chromatography (dichloromethane:methanol=15:1), the reaction solution was extracted with dichloromethane. The organic layer was washed with successive HCl and H$_2$O and dehydrated with anhydrous Na$_2$SO$_4$. It was separated by filtration and washed with dichloromethane. The combined filtrate and washings were concentrated under reduced pressure. The resultant syrup was dissolved in acetone (30 ml), mixed with Drierite®(3 g) and stirred for 1 hr. Potassium thioacetate (1.24 g) was added and the mixture was stirred at 45° C. overnight. After a completion of the reaction was confirmed by thin layer chromatography (dichloromethane:methanol=15:1), the reaction solution was filtered through Celite and washed with dichloromethane. The combined filtrate and washings were concentrated under reduced pressure. The resultant syrup was subjected to silica gel column chromatography (Wakogel C-200) using 120/1 dichloromethane/methanol an eluting solvent to afford Compound 29 (870 mg, 56.3%).

$C_{34}H_{47}NO_2S_2$ 853.86

$[\alpha]_D = +17.77°$ (c=0.664, chloroform)

IR$\nu^{Film}_{max}$cm$^{-1}$ 3700–3200 (NH), 3100–2900 (CH), 1750 (ester), 1680, 1540 (amide)

270 MHz $^1$H-NMR(CDCl$_3$)δppm:

Galactose unit 5.59(d, 1H, H-4), 5.42(d, 1H, $J_{1,2}$ 9.9 Hz, H-1), 5.29 (t, 1H, $J_{2,3}$ 9.7 Hz, H-2), 5.21(dd, 1H, $J_{3,4}$ 3.1 Hz, H-3), 2.87(dd, 1H, $J_{5,6}$ 7.5 Hz, $J_{6,6'}$14.3 Hz, H-6), 2.64(dd, 1H, $J_{5,6'}$6.6 Hz, H-6'), 2.38(s, 3H, SAc).

Neu 5 Ac unit 5.31(m, 2H, H-7,8), 4.91(ddd, 1H, $J_{3e,4}$ 4.6 Hz, $J_{3a,4}$ 11.5 Hz, $J_{4,5}$ 10.3 Hz, H-4), 4.46(dd, 1H, H-9), 4.15(dd, 1H, $J_{8,9}$ 3.3 Hz, $J_{9,9'}$11.9 Hz, H-9'), 2.72(dd, 1H, $J_{3a,3e}$ 12.6 Hz, H-3e), 1.89(s, 3H, NAc).

Others 2.19, 2.17, 2.15, 2.04, 2.03, 2.03, 1.97(7 s, 21H, 7 AcO)

S-(Methyl 5-acetamido-4,7,8,9-tetra-O-acetyl-3,5-dideoxy-D-glycero-α-D-galacto-2-nonulopyranosylonate)-(2→6)-S-(2,3,4-tri-O-acetyl-6-thio-β-D-galactopyranosyl)-(1→1)-(2R,3R,4E)-2-azido-3-benzoyloxy-4-octadecene-1-thiol (Compound 30)

Compound 29 (300 mg) was dissolved in methanol (2 ml) and the solution was cooled to −30° C. Methanol (0.3 ml) containing matallic Na (8 mg) was added dropwise and the mixture was stirred at −30° C. for 5 minutes. After a completion of the reaction was confirmed by t.l.c. (ethyl acetate), the reaction solution was concentrated at a water temperature under reduced pressure. The resultant syrup and Compound 25 (410 mg) were dissolved in N,N-dimethylformamide (4.5 ml) and stirred at 45° C. overnight in a nitrogen stream. Pyridine (4 ml) and acetic anhydride (2 ml) were added and the mixture was stirred at room temperature one day. After a completion of the reaction was confirmed by thin layer chromatography (dichloromethane:methanol=15:1), the reaction solution was concentrated under reduced pressure. The resultant syrup was subjected to silica gel column chromatography (Wakogel C-200) using 120/1 dichloromethane/methanol as an eluting solvent to afford Compound 30 (189 mg, 44%).

$C_{57}H_{82}N_4O_{11}S_2$ 1223.41

$[\alpha]_D = -26.25°$ (c=0.826, chloroform)

IR$\nu^{Film}_{max}$cm$^{-1}$ 3700–3200 (NH), 2950, 2850 (CH), 2100 (N$_3$), 1750 (ester), 1660, 1540 (amide), 710 (phenyl)

270 MHz $^1$H-NMR(CDCl$_3$)δppm:

Galactose unit 5.66(d, 1H, H-4), 5.22(t, 1H, H-2), 5.15(dd, 1H, $J_{2,3}$ 9.9 Hz, $J_{3,4}$ 3.0 Hz, H-3), 4.92(d, 1H, $J_{1,2}$ 9.5 Hz, H-1), 2.78(dd, 1H, $J_{5,6}$ 6.6 Hz, $J_{6,6'}$14.7 Hz, H-6), 2.60(dd, 1H, $H_{5,6'}$7.7 Hz, H-6').

Neu 5 Ac unit 5.38(d, 1H, $J_{5,NH}$ 8.9 Hz, NH), 5.27(m, 2H, H-7,8), 4.88(m, 1H, H-4), 4.27(dd, 1H, H-9), 3.71(s, 3H, MeO), 2.66(dd, 1H, $J_{3e,4}$ 4.4 Hz, $J_{3a,3c}$ 13.0 Hz, H-3e), 1.89(s, 3H, NAc).

Sphingosine unit 7.42–8.09(m, 5H, Ph), 5.96(dt, 1H, $J_{5,6}=J_{5,6'}$6.8 Hz, H-5), 5.76(dd, 1H, $J_{2,3}$ 3.5 Hz, $J_{3,4}$ 8.2 Hz, H-3), 5.56(dd, 1H, $J_{4,5}$ 15.4 Hz, H-4), 2.93(dd, 1H, $J_{1,2}$ 5.8 Hz, $J_{1,1'}$14 Hz, H-1), 2.71(m, 1H, H-1'), 1.24(s, 22H, 11CH$_2$), 0.88(t, 3H, CH$_3$).

Others 2.19, 2.15, 2.13, 2.07, 2.03, 2.02, 1.96(7 s, 21H, 7 AcO)

S-(Methyl 5-acetamido-4,7,8,9-tetra-O-acetyl-3,5-dideoxy-D-glycero-α-D-galacto-2-nonulopyranosylonate)-(2→6)-S-(2,3,4-tri-O-acetyl-6-thio-β-D-galactopyranosyl)-(1→1)-(2R,3R,4E)-3-benzoyloxy-2-octadecanamide-4-octadecene-1-thiol (Compound 31)

Compound 30 (134 mg) was dissolved in pyridine (10 ml) and water (2 ml). After cooling to 0° C., the solution was stirred at 0° C. to w.t. for 4 days while blowing hydrogen sulfide. After a completion of the reaction was confirmed by thin layer chromatography (dichloromethane:methanol=15:1), the reaction solution was concentrated at 30° C. under reduced pressure. The resultant syrup was dissolved in dichloromethane (8 ml), WSC (63 mg) and stearic acid (94 mg) were added and the mixture was stirred at room temperature overnight. After a completion of the reaction was confirmed by thin layer chromatography (dichloromethane:methanol=15:1), the reaction solution was extracted with dichloromethane. The organic layer was washed with water and dehydrated with anhydrous $Na_2SO_4$. It was separated by filtration and washed with dichloromethane. The combined filtrate and washings were concentrated under reduced pressure. The resultant syrup was subjected to silica gel column chromatography (Wakogel C-200) using 120/1 dichloromethane/methanol as an eluting solvent to afford Compound 31 (135 mg, 84.2%).

$C_{75}H_{118}N_2O_{22}S_2$ 1463.88

$[\alpha]_D = -7.88°$ (c=0.558, chloroform)

IR$\nu^{Film}_{max}$cm$^{-1}$ 3700-3200 (NH), 2950, 2850 (CH), 1750 (ester), 1660, 1540 (amide), 710 (phenyl)

270 MHz $^1$H-NMR(CDCl$_3$)δppm:

Galactose unit 5.61(d, 1H, H-4), 5.18(dd, 1H, H-2), 5.12(dd, 1H, $J_{3,4}$ 2.8 Hz, $J_{2,3}$ 10.3 Hz, H-3), 4.70(d, 1H, $J_{1,2}$ 9.2 Hz, H-1), 2.88(dd, 1H, $J_{5,6}$ 4.8 Hz, $J_{6,6'}$12.5 Hz, H-6), 2.84(dd, 1H, $J_{5,6'}$6.8 Hz, H-6').

Neu 5 Ac unit 5.27(m, 2H, H-7,8), 4.90(m, 1H, H-4), 4.25(dd, 1H, H-9), 4.13(dd, 1H, H-9'), 3.79(s, 3H, MeO), 2.67(dd, 1H, $J_{3c,4}$ 4.2 Hz, $J_{3a,3e}$ 12.8 Hz, H-3e), 1.89(s, 3H, NAc).

Ceramide unit 7.41-8.06(m, 5H, Ph), 6.05(d, 1H, $J_{NH,2}$ 8.8 Hz, NH), 5.85 (dt, 1H, $J_{5,6}=J_{5,6'}$6.8 Hz, H-5), 5.49(dd, 1H, $J_{3,4}$7.3 Hz, $J_{4,5}$ 15.2 Hz, H-4), 4.46((m, 1H, H-2), 3.15(dd, 1H, $J_{1,2}$ 3.8 Hz, $J_{1,1'}$14.3 Hz, H-1), 2.59(dd, 1H, $J_{1',2}$ 7.7 Hz, H-1'), 1.24(s, 50H, 25CH$_2$), 0.88(t, 6H, 2CH$_3$).

Others 2.18, 2.12, 2.11, 2.04, 2.03, 2.03, 1.96(7 s, 21H, 7 AcO)

S-(5-Acetamido-3,5-dideoxy-D-glycero-α-D-galacto-2-nonulopyranosylonic acid)-(2→6)-S-(6-thio-β-D-glucopyranosyl)-(1→1)-(2R,3R,4E)-3-hydroxy-2-octadecanamid-4-octadecene-1-thiol (Compound 3)

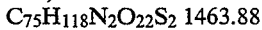

Compound 31 (100 mg) was dissolved in methanol (3 ml) and a catalytic amount of 28% sodium methylate was added, and the mixture was stirred at room temperature for 7 hrs. After completion of the reaction was confirmed by thin layer chromatography (butanol:methanol:water=4:2:1), the reaction solution was mixed with 0.2N KOH aqueous solution (2 ml) and further stirred overnight. After a completion of the reaction was confirmed by thin layer chromatography (butanol:-methanol:water=4:2:1), the reaction solution was neutralized with an ion-exchange resin, Amberlite IR-120(H$^+$) and separated by filtration, and washed with a mixed solvent of 10/10/1 chloroform/methanol/water. The combined filtrate and washings were concentrated under reduced pressure. The resultant syrup was subjected to column chromatography (Sephadex LH-20) using 10/10/1 chloroform/methanol/water as an eluting solvent to afford Compound 3 (68 mg, 94.7%).

$C_{53}H_{98}N_2O_{14}S_2$ 1051.49

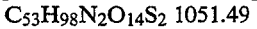

$[\alpha]_D = +15.90°$ (c=0.44, chloroform)

270 MHz $^1$H-NMR(d$_6$-DMSO: D$_2$O=49:1)δppm:

Neu 5 Ac unit 2.74(dd, 1H, $J_{3e,4}$4.8 Hz, $J_{3a,3e}$ 11.7 Hz, H-3e), 1.89(s, 3H, NAc).

Galactose unit 4.20(d, 1H, $J_{1,2}$ 8.6 Hz, H-1), 2.89(dd, 1H, $J_{6,6'}$12.1 Hz, H-6), 2.76(dd, 1H, $J_{5,6'}$6.1 Hz, H-6').

Ceramide unit 5.55(dt, 1H, $J_{5,6}=J_{5,6'}$6.6 Hz, $J_{4,5}$ 15.2 Hz, H-5), 5.37(dd, 1H, $J_{3,4}$ 6.2 Hz, H-4), 2.97(dd, 1H, $J_{1,1'}$13.2 Hz, H-1), 2.70(dd, 1H, H-1'), 2.04(t, 2H, $J_{CH_2,CH_2}$ 7.2 Hz, COCH$_2$CH$_2$), 1.24(s, 50H, 25CH$_2$), 0.85(t, 6H, 2CH$_3$)

EXAMPLE 4

S-(Methyl 5-acetamido-4,7,8,9-tetra-O-acetyl-3,5-dideoxy-D-glycero-α-D-galacto-2-nonulopyranosylonate)-(2→6)-O-(2,3,4-tri-O-acetyl-6-thio-β-D-galactopyranosyl)-(1→4)-2,3,6-tri-O-acetyl-1-S-acetyl-1-thio-β-D-glucopyranose (Compound 33)

S-(Methyl 5-acetamido-4,7,8,9-tetra-O-acetyl-3,5-dideoxy-D-glycero-α-D-galacto-2-nonulopyranosylonate)-(2→6)-O-(2,3,4-tri-O-acetyl-6-thio-β-D-galactopyranosyl)-(1→4)-2,3,6-tri-O-acetyl-D-glucopyranose (Compound 32) (500 mg) was dissolved in dichloromethane (6 ml) and 2,4,6-collidine (0.6 ml) was added. The mixture was cooled to −15° C. and methanesulfonylchloride (0.3 ml) was added. The mixture was stirred at −15° C. for 30 minutes and further stirred at room temperature for 1.5 hrs. After a completion of the reaction was confirmed by thin layer chromatography (dichloromethane:methanol=15:1), the reaction solution was extracted with dichloromethane. The organic layer was washed with successive HCl and H$_2$O and dehydrated with anhydrous Na$_2$SO$_4$. It was separated by filtration and washed with dichloromethane. The combined filtrate and washings were concentrated under reduced pressure. The resultant syrup was dissolved in acetone (10 ml), mixed with Drierite®(1 g) and stirred for 1 hr. Potassium thioacetate (315 mg) was added and the mixture was stirred at 45° C. overnight. After a completion of the reaction was confirmed by thin layer chromatography (dichloromethane:methanol=15:1), the reaction solution was filtered through Celite and washed with dichloromethane. The combined filtrate and washings were concentrated under reduced pressure. The resultant syrup was subjected to silica gel column chromatography (Wakogel C-200) using 100/1 dichloromethane/methanol as an eluting solvent to afford Compound 33 (279 mg, 53%).

$C_{46}H_{63}NO_{28}S_2$ 1142.12

$[\alpha]_D = +0.26$ (c=0.75, chloroform)

IR$\nu^{Film}_{max}$cm$^{-1}$ 3700-3200 (NH), 3100-2900 (CH), 1750 (ester), 1670, 1540 (amide)

270 MHz $^1$H-NMR(CDCl$_3$)δppm:

Lactose unit 5.52(d, 1H, $J_{3',4'}$2.9 Hz, H-4'), 5.23(d, 1H, $J_{1,2}$ 10.4 Hz, H-1), 5.07(t, 1H, H-3), 5.06(t, 1H, $J_{2,3}$ 9.5 Hz, H-2), 5.00(dd, 1H, $J_{2',3'}$10.3 Hz, H-3'), 4.70(d, 1H, $J_{1',2'}$73 Hz, H-1'), 2.81(dd, 1H, $H_{5',6'a}$ 7.2 Hz, $J_{6'a,6'b}$ 14.5

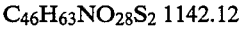

Hz, H-6′a), 2.55(dd, 1H, J$_{5',6'b}$ 7.2 Hz, H-6′b), 2.37(s, 3H, SAc).

Neu 5 Ac unit 5.39(d, 1H, J$_{NH,5}$ 8.1 Hz, NH), 5.23(m, 1H, H-8), 4.93(m, 1H, H-4), 4.47(dd, 1H, H-9), 4.27(dd, 1H, J$_{8,9'}$ 2.9 Hz, J$_{9,9'}$ 12.4 Hz, H-9′), 3.86(s, 3H, MeO), 2.73(dd, 1H, J$_{3e,r}$ 4.6 Hz, J$_{3a,3e}$ 12.8 Hz, H-3e), 1.90(s, 3H, NAc).

Others 2.19, 2.18, 2.14, 2.08, 2.05, 2.05, 2.04, 2.03, 2.02, 1.94

S-(Methyl 5-acetamido-4,7,8,9-tetra-O-acetyl-3,5-dideoxy-D-glycero-α-D-galacto-2-nonulopyranosylonate)-(2→6)-O-(2,3,4-tri-O-acetyl-6-thio-β-D-galactopyranosyl)-(1→4)-S-(2,3,6-tri-O-acetyl-β-D-glucopyranosyl)-(1→1)-(2R,3R,4E)-2-azido-3-benzoyloxy-4-octadecene-1-thiol (Compound 34)

Compound 33 (250 mg) was dissolved in methanol (2 ml) and the solution was cooled to −30° C. Methanol (0.2 ml) containing metallic Na (5 mg) was added dropwise and the mixture was stirred at −30° C. for 5 minutes. After a completion of the reaction was confirmed by t.l.c. (ethyl acetate), the reaction solution was concentrated at a water temperature under reduced pressure. The resultant syrup and Compound 25 (255 mg) were dissolved in N,N-dimethylformamide (4 ml) and stirred at 45° C. overnight in a nitrogen stream. Pyridine (4 ml) and acetic anhydride (2 ml) were added and the mixture was stirred at room temperature one day. After a completion of the reaction was confirmed by thin layer chromatography (dichloromethane:methanol=15:1), the reaction solution was concentrated under reduced pressure. The resultant syrup was subjected to silica gel column chromatography (Wakogel C-200) using 100/1 dichloromethane/methanol as an eluting solvent to afford Compound 34 (124 mg, 37.6%).

C$_{57}$H$_{82}$N$_4$O$_{11}$S$_2$ 1511.67

[α]$_D$= −34.95° (c=0.618, chloroform)

IRν$^{Film}_{max}$cm$^{-1}$ 3700–3200 (NH), 2950, 2850 (CH), 2100 (N$_3$), 1760 (ester), 1670, 1540 (amide), 720 (phenyl)

270 MHz $^1$H-NMR(CDCl$_3$)δppm:

Lactose unit 5.51(d, 1H, H-4′), 5.21(t, 1H, J$_{2,3}$=J$_{3,4}$ 9.3 Hz, H-3), 4.97(t, 1H, H-2), 4.68(d, 1H, J$_{1',2'}$ 6.8 Hz, H-1′), 4.54(d, 1H, J$_{1,2}$ 9.9 Hz, H-1), 2.76(m, 1H, H-6′a), 2.62(dd, 1H, J$_{5',6'b}$ 8.4 Hz, J$_{6'a,6'b}$ 14.3 Hz, H-6′b).

Neu 5 Ac unit 4.93(m, 1H, H-4), 4.26(dd, 1H, J$_{8,9}$ 2.9 Hz, J$_{9,9'}$ 12.6 Hz, H-9), 4.15(dd, 1H, J$_{8,9'}$ 4.2 Hz, H-9′), 3.83(s, 3H, MeO), 2.71(dd, 1H, J$_{3e,4}$ 4.6 Hz, J$_{3a,3e}$ 12.8 Hz, H-3e), 1.87(s, 3H, NAc).

Sphingosine unit 7.40–8.05(m, 5H, Ph), 5.93(dt, 1H, J$_{4,5}$ 15.4 Hz, J$_{5,6}$=J$_{5,6'}$ 6.6 Hz, H-5), 5.67(dd, 1H, J$_{2,3}$ 3.7 Hz, J$_{3,4}$ 8.3 Hz, H-3), 5.52(dd, 1H, H-4), 2.79(dd, 1H, J$_{1,2}$ 6.4 Hz, J$_{1,1'}$ 14.5 Hz, H-1), 2.52(dd, 1H, J$_{1',2}$ 7.7 Hz, H-1′), 1.21(s, 22H, 11CH$_2$), 0.85(t, 3H, CH$_3$).

Others 2.16, 2.15, 2.11, 2.03, 2.03, 2.01, 2.01, 2.01, 1.91, 1.90(10 s, 30H, 10 AcO)

S-(Methyl 5-acetamido-4,7,8,9-tetra-O-acetyl-3,5-dideoxy-D-glycero-α-D-galacto-2-nonulopyranosylonate)-(2→6)-O-(2,3,4-tri-O-acetyl-6-thio-β-D-galactopyranosyl)-(1→4)-S-(2,3,6-tri-O-acetyl-α-D-glucopyranosyl)-(1→1)-(2R,3R,4E)-3-benzoyloxy-2-octadecanamid-4-octadecene-1-thiol (Compound 35)

Compound 34 (108 mg) was dissolved in pyridine (7.5 ml) and water (1.5 ml). After cooling to 0° C., the solution was stirred for 3 days until it returned to room temperature while blowing hydrogen sulfide. After a completion of the reaction was confirmed by thin layer chromatography (dichloromethane:methanol=15:1), the reaction solution was concentrated at 30° C. under reduced pressure. The resultant syrup was dissolved in dichloromethane (6 ml), WSC (41 mg) and stearic acid (61 mg) were added and the mixture was stirred at room temperature for 5 hrs. After completion of the reaction was confirmed by thin layer chromatography (dichloromethane:methanol=15:1), the reaction solution was extracted with dichloromethane. The organic layer was washed with water and dehydrated with anhydrous Na$_2$SO$_4$. It was separated by filtration and washed with dichloromethane. The combined filtrate and washings were concentrated under reduced pressure. The resultant syrup was subjected to silica gel column chromatography (Wakogel C-200) using 100/1 dichloromethane/methanol as an eluting solvent to afford Compound 35 (96 mg, 76.7%).

C$_{87}$H$_{134}$N$_2$O$_{30}$S$_2$ 1752.14

[α]$_D$= −11.74° (c=1.124, chloroform)

IRν$^{Film}_{max}$cm$^{-1}$ 3700–3200 (NH), 2950, 2850 (CH), 1760 (ester), 1670, 1540 (amide), 720 (phenyl)

270 MHz $^1$H-NMR(CDCl$_3$)δppm:

Lactose unit 5.52(d, 1H, H-4′), 5.21(t, 1H, H-3), 5.03(m, 2H, H-2′,3′), 4.95(t, 1H, J$_{2,3}$ 9.8 Hz, H-2), 4.68(d, 1H, J$_{1',2'}$ 7.1 Hz, H-1′), 4.49(d, 1H, J$_{1,2}$ 10.0 Hz, H-1), 2.81(dd, 1H, J$_{5',6'a}$ 6.8 Hz, J$_{6'a,6'b}$ 14.5 Hz, H-6′a), 2.54(dd, 1H, J$_{5',6'b}$ 7.3 Hz, H-6′b).

Neu 5 Ac unit 5.27(m, 2H, H-7,8), 4.95(m, 1H, H-4), 4.28(dd, 1H, H-9), 4.16(dd, 1H, J$_{8,9'}$ 4.3 Hz, J$_{9,9'}$ 12.6 Hz, H-9′), 3.85(s, 3H, MeO), 2.73(dd, 1H, J$_{3e,4}$ 4.3 Hz, J$_{3a,3e}$ 12.6 Hz, H-3e), 1.90(s, 3H, NAc).

Ceramide unit 7.29–8.05(m, 5H, Ph), 5.88(d, 1H, J$_{NH,2}$ 8.9 Hz, NH), 5.86 (dt, 1H, J$_{5,6}$=J$_{5,6'}$ 6.6 Hz, H-5), 5.61(t, 1H, H-3), 5.48(dd, 1H, J$_{2,4}$ 7.1 Hz, J$_{4,5}$ 15.2 Hz, H-4), 3.00(dd, 1H, J$_{1,2}$ 4.9 Hz, J$_{1,1'}$ 13.7 Hz, H-1), 2.87 (dd, 1H, J$_{1',2}$ 7.5 Hz, H-1′), 1.25(s, 50H, 25CH$_2$), 0.88(t, 6H, 2CH$_3$).

Others 2.18, 2.18, 2.13, 2.05, 2.04, 2.04, 2.04, 2.02, 1.99, 1.94

S-(5-Acetamido-3,5-dideoxy-D-glycero-α-D-galacto-2-nonulopyranosylonic acid)-(2→6)-O-(6-thio-β-D-galactopyranosyl-(1→4)-S-β-D-glucopyranosyl-(1→1)-(2R,3R,4E)-3-hydroxy-2-octadecanamid-4-octadecene-1-thiol (Compound 4)

Compound 35 (70 mg) was dissolved in methanol (2.5 ml) and a catalytic amount of 28% sodium methylate was added, and the mixture was stirred at room temperature for 8 hrs. After a completion of the reaction was confirmed by thin layer chromatography (butanol:ethanol:water=4:2:1), the reaction solution was mixed with 0.2N KOH aqueous solution (2 ml) and further stirred overnight. After a completion of the reaction was confirmed by thin layer chromatography (butanol:ethanol:water=4:2:1), the reaction solution was neutralized with an ion-exchange resin, Amberlite IR-120(H+) and separated by filtration, and washed with a mixed solvent of 10/10/1 chloroform/methanol/water. The combined filtrate and washings were concentrated under reduced pressure. The resultant syrup was subjected to column chromatography (Sephadex LH-20) using 10/10/1 chloroform/methanol/water as an eluting solvent to afford Compound 4 (48 mg, quantitative).

C$_{59}$H$_{108}$N$_2$O$_{19}$S$_2$ 1213.63

[α]$_D$= −12.50° (c=0.40, chloroform:methanol=1:1)

270 MHz $^1$H-NMR(d$_6$-DMSO: D$_2$O=49:1)δppm:

Neu 5 Ac unit 1.89(s, 3H, NAc).

Lactose unit 4.30(d, 1H, $J_{1',2'}$ 9.7 Hz, H-1'), 4.25(d, 1H, H-1).

Ceramide unit 5.54(dt, 1H, H-5), 5.36(dd, 1H, $J_{3,4}$ 5.9 Hz, $J_{4,5}$ 15.6 Hz, H-4), 2.05(t, 2H, $J_{CH_2,CH_2}$ 7.1 Hz, COCH$_2$CH$_2$), 1.24(s, 50H, 25CH$_2$), 0.85t, 6H, 2CH$_3$).

Others 2.91–3.00(m, 2H, Cer-1, Gal-6), 2.64–2.79(m, 3H, Neu 5Ac-3e, Cer-1', Gal-6')

EXAMPLE 5

O-(3,4,6-Tri-O-acetyl-2-deoxy-2-phthalimide-β-D-glucopyranosyl)-(1→1)-(2S,3R,4E)-2-azido-3-O-benzoyl-4-octadecene-1,3-diol (Compound 38)

(2S,3R,4E)-2-Azido-3-O-benzoyl-4-octadecene-1,3-diol (Compound 37) (200 mg) was dissolved in dichloromethane (1 ml), Molecular Sieves 4A (100 mg), silver carbonate (260 mg) and silver perchlorate (200 mg) were added and the mixture was stirred at room temperature in the dark overnight. This solution was cooled to 0° C. To the cooled solution was a solution of 3,4,6-tri-O-acetyl-2-deoxy-2-phthalimide-D-glucopyranosyl bromide (Compound 36) (400 mg) dissolved in dichloromethane (1 ml) which was mixed with Molecular Sieves 4A (100 mg) and stirred at room temperature overnight. The solution was stirred further one day in the dark. After a completion of the reaction was confirmed by thin layer chromatography (ethyl acetate:hexane=1:1), the solid material was separated by filtration through Celite and washed with dichloromethane. The combined filtrate and washings were concentrated under reduced pressure. The resultant syrup was subjected to silica gel column chromatography (Wakogel C-200) using ½ ethyl acetate/hexane as an eluting solvent to afford Compound 38 (230 mg, 58.3%).

C$_{45}$H$_{58}$N$_4$O$_{12}$ 846.98

$[\alpha]_D = +0.30$ (c=0.658, chloroform)

IR$\nu^{Film}_{max}$cm$^{-1}$ 2950, 2850 (CH), 2100 (N$_3$), 1750 (ester), 720 (phenyl)

270 MHz $^1$H-NMR(CDCl$_3$)δppm:

GlcNphth unit 5.78(dd, 1H, $J_{3,4}$ 9.3 Hz, $J_{2,3}$ 11 Hz, H-3), 5.44(d, 1H, $J_{1,2}$ 8.2 Hz, H-1), 5.19(t, 1H, $J_{4,5}$ 9.7 Hz, H-4), 4.37(dd, 1H, H-2), 4.28(dd, 1H, $J_{5,6}$ 4.6 Hz, $J_{6,6'}$ 12.5 Hz, H-6), 4.15(dd, 1H, $J_{5,6'}$ 2.4 Hz, H-6'), 2.07, 2.03, 1.87, (3 s, 9H, 3 AcO).

Sphingosine unit 5.70(m, 1H, H-5), 5.42(m, 1H, H-4), 1.22–1.26(m, 22H, 11CH$_2$), 0.88(t, 3H, CH$_3$).

Others 7.40–8.04(m, 9H, 2 Ph)

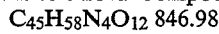

O-(2-Acetamido-2-deoxy-β-D-glucopyranosyl-(1→1)-(2S,3R,4E)-2-azido-4-octadecene-1,3-diol (Compound 39)

Compound 38 (250 mg) was dissolved in methanol (5 ml) and a catalytic amount of 28% sodium methylate was added, and the mixture was stirred at 45° C. overnight. After a completion of the reaction was confirmed by thin layer chromatography (dichloromethane:methanol=10:1), the reaction solution was neutralized with an ion-exchange resin, Amberlite IR-120(H+) and separated by filtration, and washed with methanol. The combined filtrate and washings were concentrated under reduced pressure. The resultant syrup was dissolved in 95% ethanol (3 ml) and mixed with hydrazine monohydrate (0.057 ml). The mixture was heated under reflux at 85° C. for 5 hrs. After a completion of the reaction was confirmed by thin layer chromatography (dichloromethane:methanol=10:1 ), the reaction solution was cooled to 0° C., filtered through Celite and washed with methanol. The combined filtrate and washings were concentrated under reduced pressure. The resultant syrup was dissolved in methanol (5 ml), anhydrous acetic acid (1 ml) was added and the mixture was stirred at room temperature overnight. After a completion of the reaction was confirmed by thin layer chromatography (dichloromethane:methanol=10:1), pyridine was added and the reaction solution was concentrated under reduced pressure. The resultant syrup was subjected to silica gel column chromatography (Wakogel C-200) using 10/1 dichloromethane/methanol as an eluting solvent to afford Compound 39 (147 mg, 94.2%).

C$_{26}$H$_{48}$N$_4$O$_7$ 528.69

$[\alpha]_D = -13.93°$ (c=0.99, methanol)

270 MHz $^1$H-NMR(CD$_3$OD)δppm:

GlcNAc unit 4.44(d, 1H, $J_{1,2}$ 8.2 Hz, H-1), 3.93(dd, 1H, $J_{5,6}$ 6.4 Hz, $J_{6,6'}$ 10.6 Hz, H-6), 3.88(dd, 1H, $J_{5,6'}$ 1.8 Hz, H-6), 1.98(S, 3H, NAc)

Sphingosine unit 5.74(dt, 1H, $J_{5,6}=J_{5,6'}$ 6.6 Hz $J_{4,5}$ 15.2 Hz, H-5), 5.49(dd, 1H, $J_{3,4}$ 7.3 Hz, H-4), 1.29(s, 22H, 11CH$_2$), 0.90(t, 3H, CH$_3$)

O-[2-Acetamido-2-deoxy-6-O-(p-toluenesulfonyl)-β-D-glucopyranosyl]-(1=1)-(2S,3R,4E)-2-azido-4octadecene-1,3-diol (Compound 40)

Compound 39 (100 mg) was dissolved in pyridine (3 ml and cooled to 0° C., and p-toluenesulfonylchloride (80 mg) was added. The mixture was stirred at 0° C. for 4 hrs. p-Toluenesulfonylchloride (64 mg) was further added and stirred at 0° C. for further 6 hrs. After a completion of the reaction was confirmed by thin layer chromatography (dichloromethane:methanol=10:1), methanol was added and the reaction solution was concentrated under reduced pressure. The resultant syrup was subjected to silica gel column chromatography (Wakogel C-300) using 15/1 dichloromethane/methanol as an eluting solvent to afford Compound 40 (83 mg, 64.2%).

C$_{33}$H$_{54}$N$_4$O$_9$S 682.87

$[\alpha]_D = -21.34°$ (c=0.534, chloroform)

IR$\nu^{Film}_{max}$cm$^{-1}$ 3600–3100 (NH, OH), 2950, 2850 (CH), 2100 (N$_3$), 1650, 1550 (amide)

270 MHz $^1$H-NMR(CD$_3$OD)δppm:

GlcNAc unit 7.44–7.83(m, 4H, Ph), 4.42(d, 1H, $J_{1,2}$ 8.3 Hz, H-1), 2.47(s, 3H, CH$_3$Pb), 1.98(s, 3H, NAc).

Sphingosine unit 5.75(dt, 1H, $J_{5,6}=J_{5,6'}$ 6.6 Hz, H-5), 5.51(dd, 1H, $J_{3,4}$ 7.4H, $J_{4,5}$ 15.4 Hz, H-4), 1.29(s, 22H, 11CH$_2$), 0.91(t, 3H, CH$_3$)

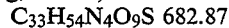

S-(Methyl 5-acetamido-4,7,8,9-tetra-O-acetyl-3,5-dideoxy-D-glycero-α-D-galacto-2-nonulopyranosylonate)(2→6)-O-(2-acetamido-2-deoxy-β-D-glucopyranosyl)-(1→1)-(2S,3R,4E)-2-azido-4-octadecene-1,3-diol (Compound 42)

Compound 40 (83 mg) and sodium salt of methyl 5-acetamido- 4,7,8,9-tetra-O-acetyl-3,5-dideoxy-2-thio-D-glycero-α-D-galactose-2-nonulopyranosylonate were dissolved in N,N-dimethylformamide (3 ml) and stirred at 45° C. overnight in a nitrogen stream. After a completion of the reaction was confirmed by thin layer chromatography (dichloromethane:methanol=15:1), the reaction solution was concentrated under reduced pressure. The resultant syrup was subjected to silica gel column chromatography (Wakogel C-300) using 20/1 dichloromethane/methanol as an eluting solvent to afford Compound 42 (94 mg, 76.0%).

$C_{46}H_{75}N_5O_{18}S$ 1018.18

$[\alpha]_D = +13.38°$ (c=0.762, chloroform)

$IR\nu^{Film}{}_{max}cm^{-1}$ 3600-3100 (NH, OH), 2900, 2850 (CH), 2100 ($N_3$), 1730 (ester), 1650, 1550 (amide)

270 MHz $^1H$-NMR($CDCl_3$)$\delta$ppm:

GlcNAc unit 6.75(d, 1H, NH), 4.56(d, 1H, $J_{1,2}$ 7.3 Hz, H-1), 2.87(dd, 1H, $J_{5,6}$ 9.0 Hz, $5_{6,6'}$ 13.9 Hz, H-6).

Neu 5 Ac unit 6.04(d, 1H, $J_{NH,5}$ 9.7 Hz, NH), 5.42(m, 1H, H-8), 5.30 (dd, 1H, H-7), 4.85(ddd, 1H, $J_{3e,4}$ 4.8 Hz, $J_{3a,4}$ 11.4 Hz, $J_{4,5}$ 10.3 Hz, H-4), 3.81(s, 3H, MeO), 2.71(dd, 1H, $J_{3a,3e}$ 12.8 Hz, H-3e), 2.19, 2.16, 2.05, 2.03(4 s, 12H, 4 AcO).

Sphingosine unit 5.79(dt, 1H, $J_{5,6}=J_{5,6'}$ 6.6 Hz, $J_{4,5}$ 15.4 Hz, H-5), 5.51(dd, 1H, $J_{3,4}$ 7.3 Hz, H-4), 1.26(s, 22H, 11$CH_2$), 0.88(t, 3H, $CH_3$).

Others 2.02, 1.87, (2 s, 6H, 2 NAc)

What is claimed is:

1. A thioglycoside analog of gangliosides represented by the formula

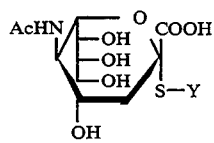

in which Y represents a radical having a formula selected from the group consisting of

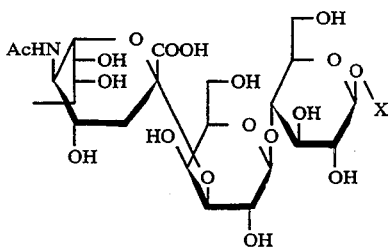

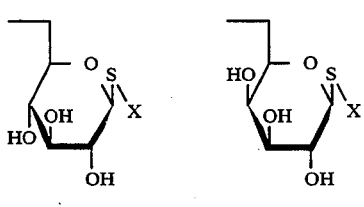

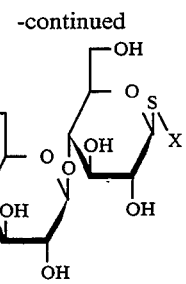

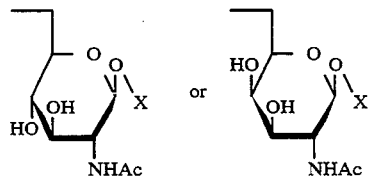

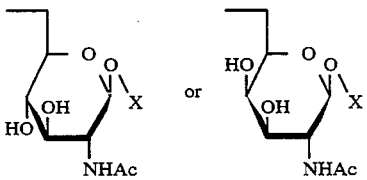

and x represents a radical of the formula

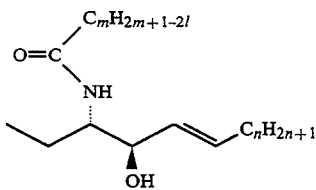

wherein m is an integer of 15 to 25, l is an integer of 0 to 3 and n is an integer of 11 to 15.

2. A thioglycoside analog of gangliosides of claim 1 wherein m is 15-25, straight chain; l is 0-3; and n is 13 or 15, straight chain.

3. A thioglycoside analog of gangliosides of claim 1 represented by the formula

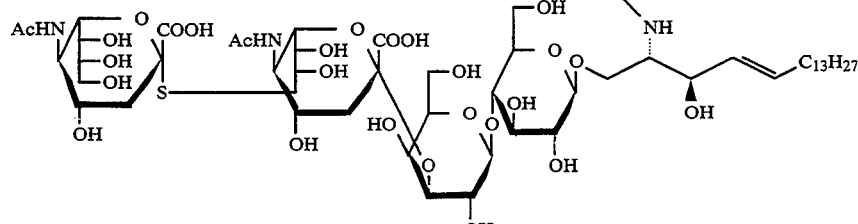

4. A thioglycoside analog of gangliosides of claim 1 represented by the formula

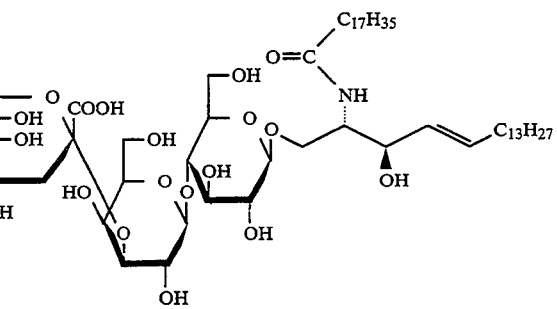

5. A thioglycoside analog of gangliosides of claim 1 represented by the formula

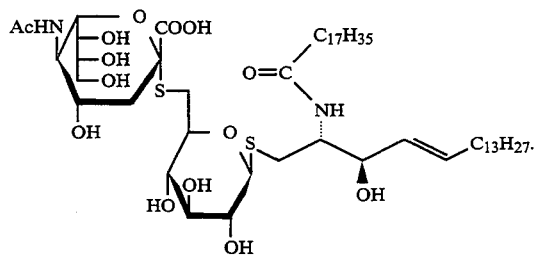

7. A thioglycoside analog of gangliosides of claim 1 represented by the formula
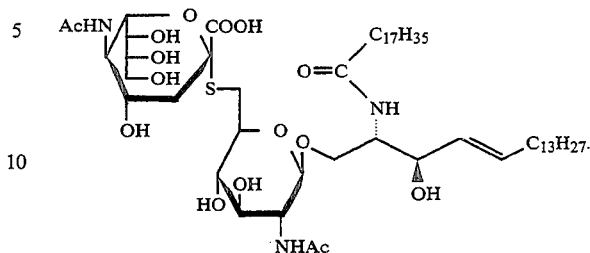
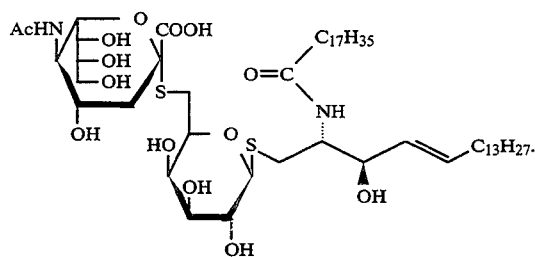
6. A thioglycoside analog of gangliosides of claim 1 represented by the formula
8. A thioglycoside analog of gangliosides of claim 1 represented by the formula
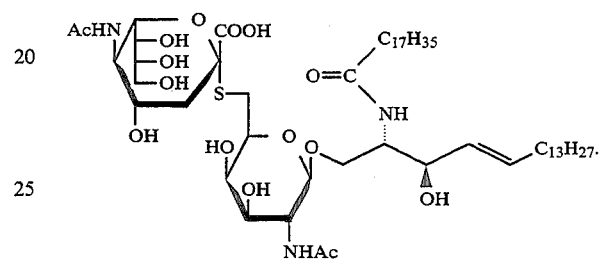
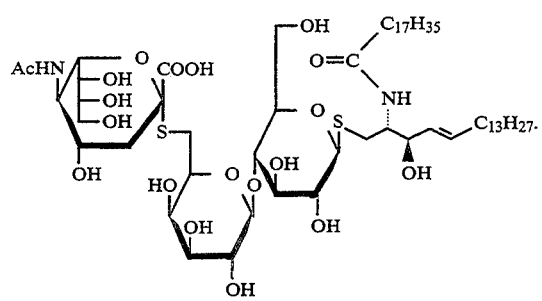
* * * * *

UNITED STATES PATENT AND TRADEMARK OFFICE
CERTIFICATE OF CORRECTION

PATENT NO. : 5,380,829
DATED : January 10, 1995
INVENTOR(S) : Akira HASEGAWA, et al.

It is certified that error appears in the above-indentified patent and that said Letters Patent is hereby corrected as shown below:

On the title page, Item [75], the inventorship should read:

--Akira Hasegawa; Makoto Kiso; both of Gifu, Japan--

Signed and Sealed this

Eleventh Day of April, 1995

*Attest:*

BRUCE LEHMAN

*Attesting Officer*     *Commissioner of Patents and Trademarks*